US012048518B2

(12) United States Patent
Semenov

(10) Patent No.: US 12,048,518 B2
(45) Date of Patent: Jul. 30, 2024

(54) INDIVIDUALLY WEARABLE ELECTROMAGNETIC SENSING (iwEMS) SYSTEM AND METHOD FOR NON-INVASIVE ASSESSMENT OF TISSUE BLOOD AND OXYGEN CONTENT

(71) Applicant: Serguei Semenov, Vienna (AT)

(72) Inventor: Serguei Semenov, Vienna (AT)

(73) Assignee: Serguei Semenov, Vienna (AT)

( * ) Notice: Subject to any disclaimer, the term of this patent is extended or adjusted under 35 U.S.C. 154(b) by 451 days.

(21) Appl. No.: 17/482,105

(22) Filed: Sep. 22, 2021

(65) Prior Publication Data

US 2022/0087558 A1 Mar. 24, 2022

Related U.S. Application Data

(60) Provisional application No. 63/204,261, filed on Sep. 22, 2020.

(51) Int. Cl.
*A61B 5/024* (2006.01)
*A61B 5/00* (2006.01)
*A61B 5/145* (2006.01)

(52) U.S. Cl.
CPC ...... *A61B 5/02438* (2013.01); *A61B 5/14542* (2013.01); *A61B 5/7246* (2013.01)

(58) Field of Classification Search
None
See application file for complete search history.

(56) References Cited

U.S. PATENT DOCUMENTS

| 6,993,379 B1 * | 1/2006 | Kroll | A61B 5/29 |
| | | | 600/509 |
| 9,072,449 B2 | 7/2015 | Semenov | |
| 9,414,749 B2 | 8/2016 | Semenov | |
| 9,414,763 B2 | 8/2016 | Semenov | |

(Continued)

OTHER PUBLICATIONS

Semenov S., Huynh T., Williams T., Nicholson B. and A. Vasilenko "Dielectric properties of brain tissue in acute Ischemic stroke: experimental study on swine", Bioelectromagnetics, 2017, 38:158-163, DOI:10.1002/bem.22024, 6 pages.

(Continued)

*Primary Examiner* — William J Levicky
*Assistant Examiner* — Willow Grace Welch
(74) *Attorney, Agent, or Firm* — Potomac Law Group, PLLC; Reza Mollaaghababa; Amanda Y. Baker

(57) ABSTRACT

A system includes at least one physiological sensor, at least one radiation source, at least one radiation detector, and a digital processor. The physiological sensor is configured to monitor a circulatory physiological parameter of a subject and to generate at least one physiological signal indicative of the monitored physiological parameter. The at least one radiation source is configured to irradiate a tissue portion with electromagnetic radiation. The at least one radiation detector is configured to detect at least a portion of the irradiating radiation transmitted through or reflected by the tissue portion and to generate at least one detected radiation signal. The digital processor is configured to receive the physiological and detected radiation signals and process the signals to derive information regarding the at least one physiological condition within the target tissue.

20 Claims, 14 Drawing Sheets

(56) References Cited

U.S. PATENT DOCUMENTS

| | | |
|---|---|---|
| 9,414,764 B2 | 8/2016 | Semenov |
| 9,675,254 B2 | 6/2017 | Semenov |
| 9,675,255 B2 | 6/2017 | Semenov |
| 9,724,010 B2 | 8/2017 | Semenov |
| 9,924,873 B2 | 3/2018 | Semenov |
| 10,492,700 B2 | 12/2019 | Semenov |
| 10,921,361 B2 | 2/2021 | Semenov |
| 10,980,421 B2 | 4/2021 | Semenov |
| 10,980,435 B2 | 4/2021 | Semenov |
| 11,253,164 B2 | 2/2022 | Semenov et al. |
| 11,344,216 B2 | 5/2022 | Semenov et al. |
| 11,350,842 B2 | 6/2022 | Semenov et al. |
| 11,517,214 B2 | 12/2022 | Semenov |
| 11,607,134 B2 | 3/2023 | Semenov |
| 2013/0158372 A1* | 6/2013 | Haisley ............... A61B 5/1455 600/310 |
| 2013/0171599 A1* | 7/2013 | Bleich ............... A63B 24/0062 434/247 |
| 2014/0155740 A1 | 6/2014 | Semenov |
| 2014/0275944 A1* | 9/2014 | Semenov ............ A61B 5/0295 600/407 |
| 2014/0276012 A1 | 9/2014 | Semenov |
| 2015/0257648 A1 | 9/2015 | Semenov |
| 2015/0257649 A1 | 9/2015 | Semenov |
| 2016/0120469 A1* | 5/2016 | Freeman ............... A61N 1/046 600/479 |
| 2016/0256109 A1 | 9/2016 | Semenov |
| 2016/0262623 A1 | 9/2016 | Semenov |
| 2016/0345856 A1 | 12/2016 | Semenov |
| 2017/0238805 A1* | 8/2017 | Addison ............... A61B 5/7253 |
| 2017/0273563 A1 | 9/2017 | Semenov |
| 2018/0231594 A1 | 8/2018 | Semenov |
| 2018/0344165 A1 | 12/2018 | Semenov |
| 2019/0274578 A1 | 9/2019 | Semenov et al. |
| 2019/0307337 A1* | 10/2019 | Little ............... A61B 5/02141 |
| 2019/0357801 A1 | 11/2019 | Semenov et al. |
| 2019/0357802 A1 | 11/2019 | Semenov et al. |
| 2019/0357803 A1 | 11/2019 | Semenov et al. |
| 2021/0181246 A1 | 6/2021 | Semenov |
| 2021/0228085 A1 | 7/2021 | Semenov |
| 2021/0236008 A1 | 8/2021 | Semenov |
| 2022/0296120 A1 | 9/2022 | Semenov et al. |
| 2023/0116876 A1 | 4/2023 | Semenov |

OTHER PUBLICATIONS

Semenov S.Y., Kellam J.F., Althausen P., Williams T.C., Abubakar A., Bulyshev A., Sizov Y. "Microwave tomography for functional imaging of extremity soft tissues. Feasibility assessment", Phys. Med. Biol., 2007, 52, 5705-5719, 15 pages.

Semenov S., Kellam J., Nair B., Sizov Y., Nazarov A., Williams T., Nair B., Pavlovsky A., Quinn M. "Microwave tomography of extremities: 2) Functional fused imaging of flow reduction and simulated compartment syndrome.", Phys. Med. Biol., 56 (2011) 2019-2030. Online at stacks.iop.org/PMB/56/2019. doi:10.1088/0031-9155/56/7/007, 13 pages.

Semenov S Y, Svenson R H and Tatsis G P "Microwave spectroscopy of myocardial ischemia and infarction. 1. Experimental study", Annals of Biomed. Eng, 2000, 28 48-54, 7 pages.

Semenov S Y, Svenson R H, Posukh V G, Nazarov A G, Sizov Y E, Kassel J and Tatsis G P "Dielectric spectroscopy of canine myocardium during ischemia and hypoxia at frequency spectrum from 100KHz to 6GHz", IEEE Trans. MI, 2002, 21 703-7, 5 pages.

Semenov S.Y. "Microwave Tomography: Review of the Progress towards Clinical applications", Phil. Trans. R. Soc. A, 2009 367, 3021-3042. doi: 10.1098/rsta.2009.0092, 23 pages.

\* cited by examiner

INDIVIDUALLY WEARABLE ELECTROMAGNETIC SENSING (iwEMS) SYSTEM AND METHOD FOR NON-INVASIVE ASSESSMENT OF TISSUE BLOOD AND OXYGEN CONTENT

RELATED APPLICATIONS

The present application claims priority to a provisional U.S. patent application having an application No. 63/204,261 filed on Sep. 22, 2020, which is incorporated by reference in its entirety herein.

TECHNICAL FIELD

The following relates to a system and method for electromagnetically sensing biological tissues and more particularly to electromagnetically sensing biological tissues for non-invasively assessing blood content, oxygenation status, and viability of biological tissues.

BACKGROUND

Hypoxia is a condition in which tissue does not receive an adequate oxygen supply. Hypoxia may be classified as generalized (affecting the whole body) or local (affecting a region of the body). Hypoxia may lead to tissue damage or even tissue death. For example, hypoxic brain injury may occur when the brain does not receive an adequate amount of oxygen, e.g., due to a stroke. This lack of oxygen may cause a gradual death and impairment in brain cells. Unfortunately, hypoxia may also occur during routine medical procedures, e.g., when a subject is anesthetized or during childbirth.

Ischemia is a condition in which there is a restriction of blood supply to tissues which causes a shortage of oxygen that is needed to keep the affected tissue alive. Severe traumatic brain injury (TBI) may occur due to a severe blow or other traumatic injury to the head and often is associated with ischemia, which may lead to death or disability.

Since hypoxia and ischemia are often associated with brain damage or death, it is vital to measure tissue oxygenation levels during certain medical events. Devices for measuring tissue oxygenation are known in the art (e.g., finger-based oxygenation tools). Unfortunately, several of these devices use near IR technologies that are unable to provide on-line oxygenation status of deep tissues (e.g., myocardial tissue, deep brain tissue, deep skeletal muscles, etc.). This oxygenation status of deep tissues may be of critical importance during medical emergencies, during a surgical procedure that requires a subject to be anesthetized, during high-load physical conditions (e.g., during strenuous physical activity, while flying an aircraft at high levels of acceleration, during military combat, etc.). Such oxygenation status may also be of critical importance to healthcare providers at a nursing home that monitor at risk subjects.

SUMMARY

Aspects of the present disclosure address the above-referenced problems and/or others.

In one aspect, a system for non-invasive in-vivo assessment of at least one physiological condition of tissue, comprises at least one physiological sensor, at least one radiation source, at least one radiation detector, and a digital processor. The at least one physiological sensor is configured to monitor at least one circulatory physiological parameter of a subject and to generate at least one physiological signal indicative of the monitored physiological parameter. The at least one radiation source is configured to irradiate the tissue portion with electromagnetic radiation. The at least one radiation detector is configured to detect at least a portion of the irradiating radiation transmitted through or reflected by the tissue portion and to generate at least one detected radiation signal. The digital processor is configured to receive the physiological and detected radiation signals and process the signals to derive information regarding the at least one physiological condition within the target tissue.

In some embodiments of the system, the at least one radiation source and the at least one detector are incorporated in a single transceiver and the digital processor is further configured to compute a cross-correlation function of phase between a phase of the at least one detected radiation signal and the at least one physiological signal. The digital processor may be further configured to utilize the cross-correlation functions of amplitude or phase to determine whether the at least one detected radiation signal is an informative or a non-informative signal. In some embodiments, the physiological condition comprises at least one of a blood content, an oxygen content, tissue ischemia, tissue hypoxia, a tissue malignancy, and tissue viability and the malignancy may comprise a type of malignancy resulting in an increase in tissue metabolic rate and thus a higher than normal tissue blood content. In some of the embodiments of the system, the circulatory physiological parameter comprises at least one of ECG and cardiac pulse.

Furthermore, the digital processor may be configured to utilize the following relation for computing the cross-correlation function:

$$\sum_{i=1+k}^{M+k} E_i \times (E_i - E_{mean}) \times$$
$$(F_i - F_{mean}) \Big/ \left( \sqrt{\sum_{i=1+k}^{M+k} (E_i - E_{mean})^2} \times \sqrt{\sum_{i=1+k}^{M+k} (F_i - F_{mean})^2} \right)$$

wherein, $E_i$ denotes an $i^{th}$ reading of digitized electromagnetic radiation signal (for example; an amplitude or a phase), $E_{mean}$ denotes a mean of the electromagnetic signals in the sample size; $F_i$ denotes an $i^{th}$ reading of digitized physiological data signal and $F_{mean}$ denotes a mean of the physiological data signals in the sample size.

In some embodiments, the processor may be configured to compare the cross-correlation function with a reference cross-correlation function to derive the information regarding the at least one physiological condition within the target tissue and the at least one radiation source may be configured to generate radiation at a plurality of frequencies in the frequency range of about 0.01 GHz to about 10 GHz for irradiating the tissue at the plurality of frequencies. The at least one detector may be configured to detect radiation transmitted or reflected by the irradiated tissue at the plurality of frequencies to generate at least one detected radiation signal at each of the frequencies, and the digital processor may be further configured to determine a cross-correlation function associated with each of the plurality of frequencies.

Further, in some embodiments, the digital processor is configured to compare the frequency-dependent cross correlation functions to determine the at least one physiological condition and the digital processor is configured to monitor the cross-correlation functions of amplitude and cross-correlation functions of phase over two more or more cardiac cycles for deriving the information regarding the at least one physiological condition within the target tissue. The digital processor may be further configured to identify a hypoxic tissue condition based on detecting a change in the cross-correlation function of amplitude without detecting a substantial a change in the cross-correlation function of phase and may be also configured to identify an ischemic condition of the target tissue based on detecting a change in the cross-correlation function of amplitude in a direction opposite to direction of change exhibited by the cross-correlation function of amplitude in a hypoxic tissue condition as well as detecting a temporal and frequency-dependent change in the cross-correlation function of phase.

In another aspect, a method for non-invasive in-vivo assessment of at least one physiological condition of tissue, comprises monitoring at least one circulatory physiological parameter of the subject to generate one or more physiological signals, wherein the physiological parameter is indicative of temporal variations in blood circulation (e.g., blood) within a tissue portion containing a target tissue of interest, irradiating the tissue portion with electromagnetic radiation having a frequency in a range of about 0.01 GHz to about 10 GHz, detecting at least a portion of the radiation transmitted or reflected by the irradiated tissue to generate one or more detected radiation signals, synchronizing the detected radiation signals with the physiological signals, and processing the synchronized detected radiation signals and the physiological signals to obtain information regarding a physiological condition within the target tissue, wherein the processing step comprises computing a cross correlation function of amplitude between an amplitude of the at least one of the detected radiation signals and the at least one of the physiological signals.

In some embodiments, the method further comprises computing a cross correlation function of phase between a phase of the at least one of the detected radiation signal and the at least one of the physiological signals. The method may further include utilizing any of the amplitude or phase correlation functions to distinguish between informative and non-informative detected radiation signals and the physiological condition comprises at least one of blood content, oxygen content, tissue ischemia, a tissue malignancy, and tissue viability. Further, the tissue malignancy may comprise any malignant tissue with increased metabolism, resulting in higher blood content and the circulatory physiological parameter comprises at least one of ECG or cardiac pulse.

In some embodiments, the cross-correlation of the detected radiation signals and the physiological signals is performed via the following relation:

$$\sum_{i=1+k}^{M+k} E_i \times (E_i - E_{mean}) \times$$
$$(F_i - F_{mean}) / \left( \sqrt{\sum_{i=1+k}^{M+k} (E_i - E_{mean})^2} \times \sqrt{\sum_{i=1+k}^{M+k} (F_i - F_{mean})^2} \right)$$

wherein, $E_i$ denotes an $i^{th}$ reading of digitized electromagnetic radiation signal (for example: an amplitude or phase), $E_{mean}$ denotes a mean of the electromagnetic signals in the sample size; $F_i$ denotes an $i^{th}$ reading of digitized physiological data signal and $F_{mean}$ denotes a mean of the physiological data signals in the sample size.

The method may further include comparing the cross-correlation function of phase or amplitude with a reference (respective0) cross-correlation function to obtain the information about the at least one physiological condition of the target tissue. Further, the step of irradiating the issue may comprise irradiating the tissue at two or more frequencies within the frequency range of about 0.01 GH to about 10 GHz and generating the detected radiation signals for each of the two or more frequencies and the method may further include determining a cross-correlation function of phase or amplitude associated with each of the two or more frequencies. The method may also include comprising comparing the cross-correlation functions to determine the physiological condition of the tissue.

In some embodiments, the method may further comprise monitoring the cross-correlation functions of detected radiation signal amplitude and phase over two or more cardiac cycles, identifying a hypoxic condition based on observing a change in the cross-correlation function of amplitude without a substantial change in the cross-correlation function of phase over those cardiac cycles and identifying an ischemic condition based on observing a change in direction opposite to a direction of change associated with a hypoxic condition in the cross-correlation function of amplitude and a frequency and temporal-dependent change in the cross-correlation function of phase.

BRIEF DESCRIPTION OF THE DRAWINGS

Aspects of the present disclosure may take form in various components and arrangements of components, and in various steps and arrangements of steps. The drawings are only for illustration purpose of preferred embodiments of the present disclosure and are not to be considered as limiting.

Features of embodiments of the present disclosure will be more readily understood from the following detailed description take in conjunction with the accompanying drawings in which.

DETAILED DESCRIPTION

As a preliminary matter, it will readily be understood by one having ordinary skill in the relevant art ("Ordinary Artisan") that the present invention has broad utility and application. Many embodiments, such as adaptations, variations, modifications, and equivalent arrangements, will be disclosed by the embodiments described herein and fall within the scope of the present disclosure.

Accordingly, while the present disclosure provides detail in relation to one or more embodiments, it is to be understood that this disclosure is illustrative and exemplary. The detailed disclosure herein of one or more embodiments is not intended, nor is to be construed, to limit the scope of patent protection afforded the present disclosure, which scope is to be defined by the claims and the equivalents thereof.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure.

As used herein, the term "about" means plus or minus 10% of the numerical value of the number with which it is being used. Therefore, about 100 μm means in the range of 90 μm-110 μm. The term "substantially" as used herein means a variation of at most 5% or at least 2% or at most 1% relative to a complete state and/or condition.

Figure 1:
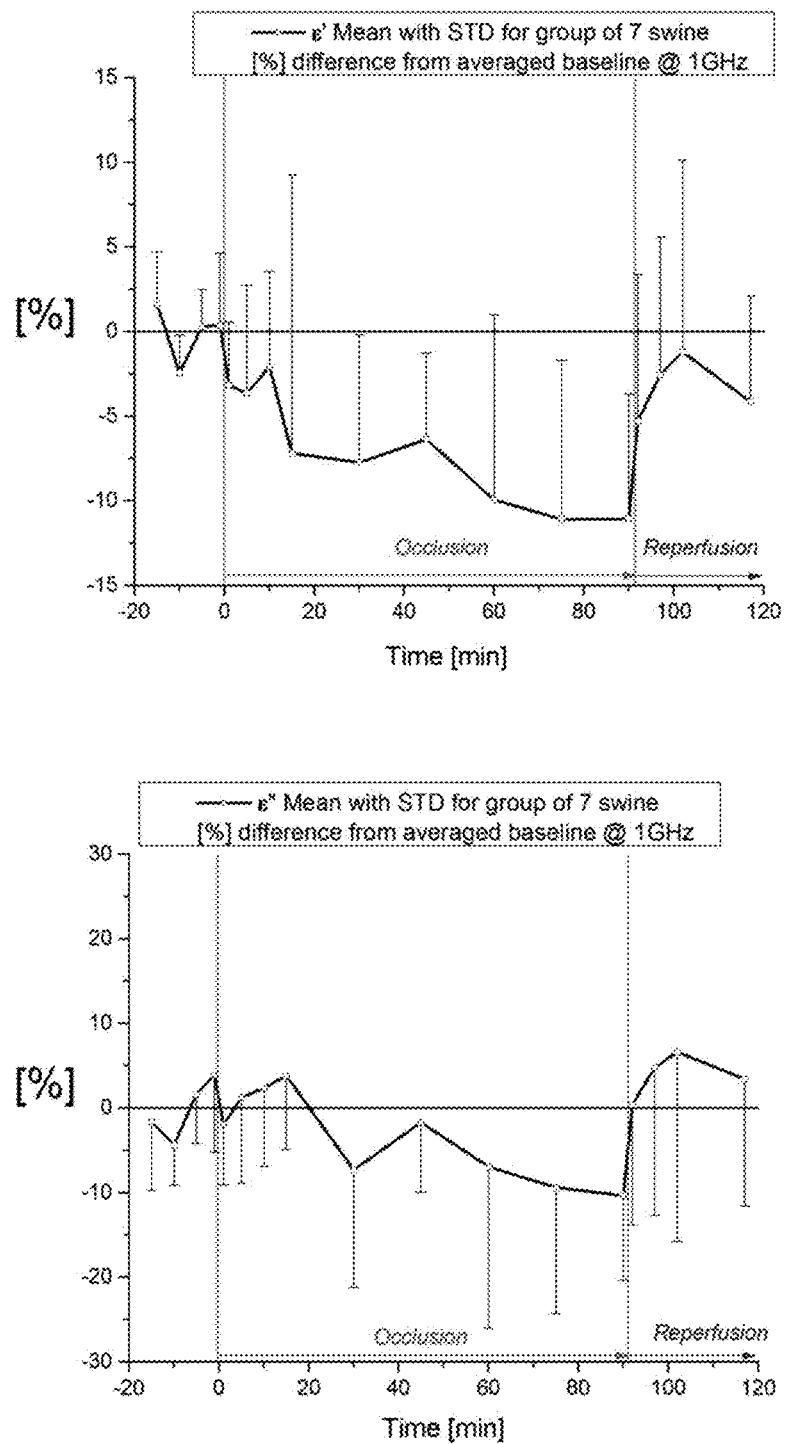
FIG. 1 depicts changes in dielectric properties (ε' and ε") of brain tissue following an induction of an ischemic stroke at time "0 min" (by an occlusion of both carotid arteries) and reperfusion at time "91 min;"
Figure 2A:
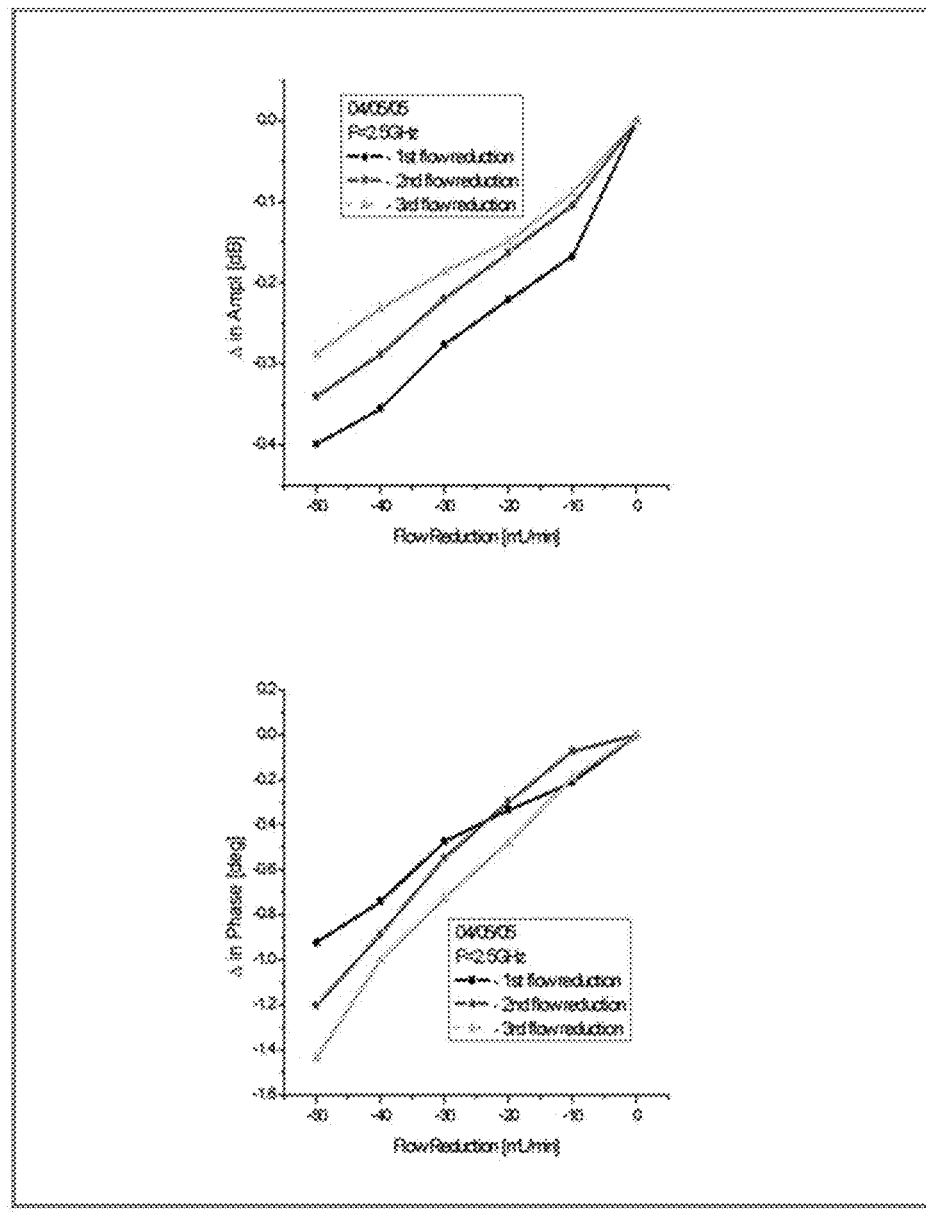
FIGS. 2A and 2B depicts changes in amplitude and phase of an electromagnetic signal transmitted through a thigh tissue due to reduction in femoral blood flow (2A) and development of compartmental injury (2B)
Figure 2B:
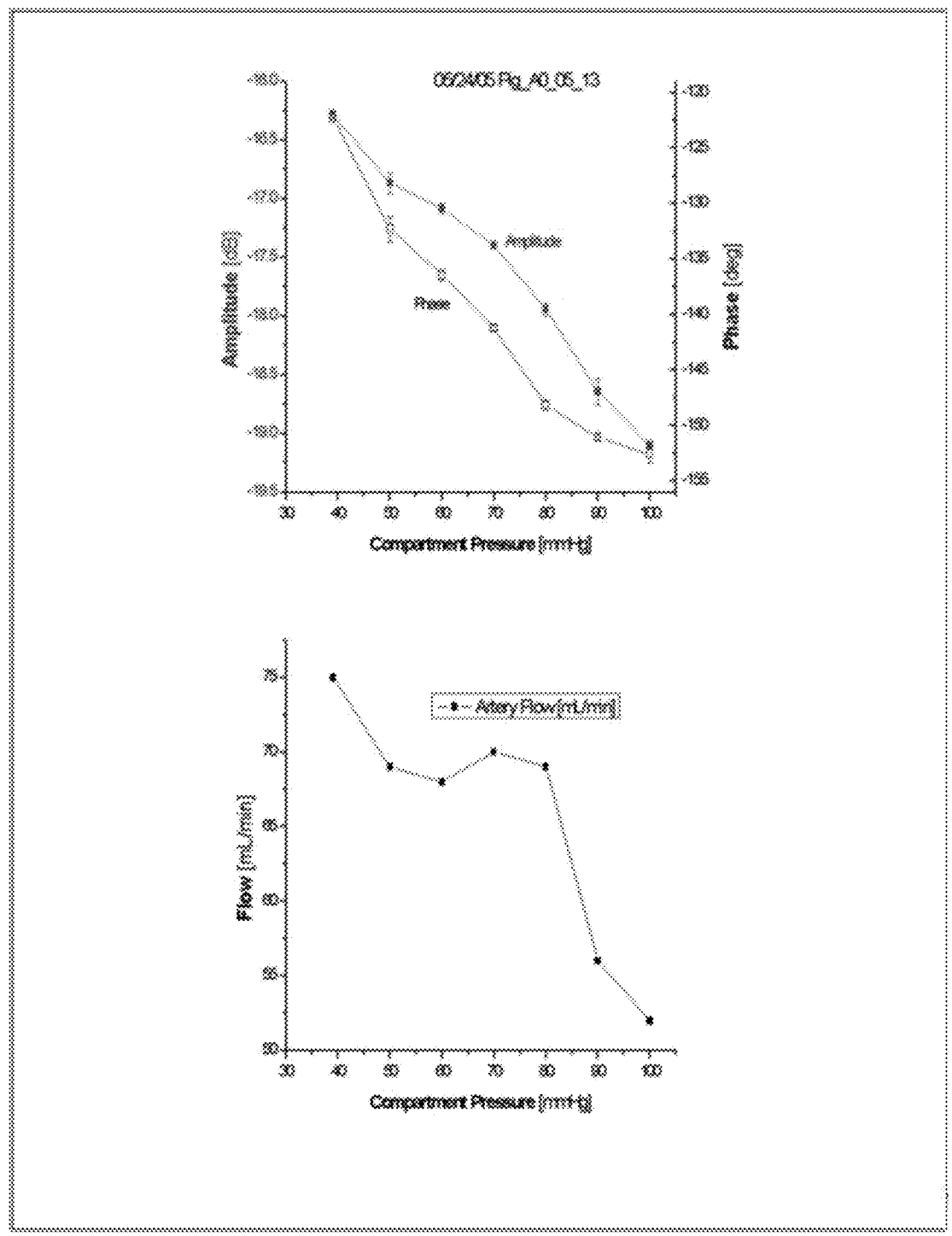

Biological tissues may be differentiated, and consequentially may be sensed or imaged, based on their dielectric properties, such as dielectric permittivity of tissue that can be indicative of the degree of polarization that an applied electric field can induce in a target tissue, e.g., when the target tissue is exposed to non-ionizing portion of the electromagnetic spectrum. For example, dielectric properties of tissues with a high-water content (e.g., muscle, etc.) and low water content (e.g., fat, bone, etc.) are significantly different. Changes in these dielectric properties may occur due to various physiological and pathological alterations (e.g., blood content, ischemia, infarction, hypoxia, malignancy, etc.). For example, the dielectric properties of brain soft tissues are sensitive to blood content (FIG. 1), dielectric properties of skeletal muscle tissues are sensitive to blood content and compartmental injury (FIGS. 2A and 2B) and dielectric properties of myocardium are sensitive to blood and oxygen content (FIGS. 3, 4A, 4B, and 4C). Such changes in the dielectric properties of a target tissue have typically a time dependence, which can allow for the potential diagnosis of development of physiological changes and/or tissue damage and subsequent action which may prove lifesaving.

The present disclosure generally relates to a system and method for monitoring of oxygenation, blood content, and viability of a tissue. In some embodiments, the present disclosure provides a system/method that includes the use of an iwEMS device for monitoring, for example, oxygenation, blood content and viability of a tissue. In some embodiments, a system according to the present teachings can include a wearable device that can be worn by a subject for measuring one or more physiological parameters associated with a target tissue. For example, in some such embodiments, the wearable device may be configured for continuous monitoring of tissue oxygenation levels, blood content and tissue viability. The measured oxygen level, blood content and viability, and temporal variations thereof, can provide vital information to a healthcare professional, e.g., a physician. For example, when a reduced oxygenation level is detected, a notification may be sent to the healthcare professional, thereby allowing the healthcare professional to take corrective measures before tissue hypoxia turns to ischemia and causes irreversible tissue damage.

As discussed in more detail below, in embodiments of systems and methods according to the present teachings, a tissue portion containing a target tissue of interest can be irradiated with electromagnetic radiation, e.g., electromagnetic radiation from non-ionizing frequency band having a frequency in a range of about 0.01 GHz to about 10 GHz, and at least a portion of the radiation transmitted and/or reflected from the tissue portion can be detected to generate a plurality of detected radiation signals. The detected radiation signals can be encoded with a plurality of physiological signals acquired at least during tissue irradiation (or a portion thereof) and the encoded signals can be analyzed to assess a physiological condition of the target tissue. As discussed in more detail below, the encoding of the detected radiation signals with the physiological signals allows distinguishing the detected radiation signals related to radiation transmitted through or reflected by the target tissue (informative information) from detected radiation signals that correspond to non-target tissue (non-informative information).

Figure 5:
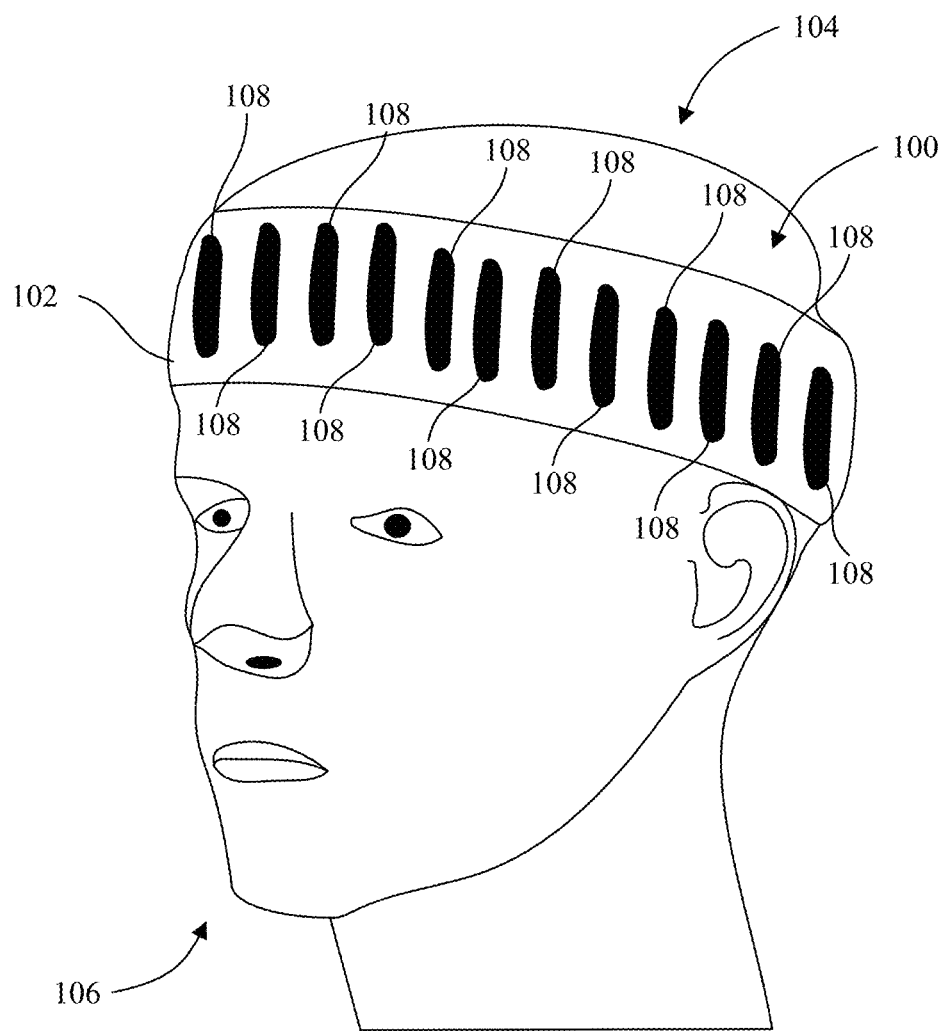
FIG. 5 depicts an individually wearable electromagnetic sensing (iwEMS) device configured to monitor brain tissue in accordance with an exemplary embodiment.

Referring now to FIG. 5, an iwEMS system 100 is shown in accordance with an exemplary embodiment. In this embodiment, the iwEMS 100 is configured to monitor brain tissue. As shown in FIG. 5, the iwEMS system 100 includes a flexible band 102 (e.g., a band fabricated from an elastic polymeric material) that can be worn around a head 104 of a subject 106, and a plurality of electromagnetic transceivers 108 that are coupled to the flexible band 102. Each electromagnetic radiation transceiver 108 includes an electromagnetic radiation source component configured to emit electromagnetic radiation and an electromagnetic radiation detector component configured to detect electromagnetic radiation. While FIG. 5 depicts the iwEMS system 100 as including a plurality of transceivers each with an electromagnetic radiation source component and an electromagnetic radiation detector component, in other embodiments, the iwEMS 100 may include individual electromagnetic radiation source(s) and individual electromagnetic radiation detector(s).

In some embodiments, the electromagnetic radiation transceivers 108 may be embedded in the band 102 while in other embodiments, they may be coupled to an external surface of the band. Further, while FIG. 5 depicts the subject 106 wearing the iwEMS 100 around their head, in other embodiments, the subject 106 may wear the iwEMS 100 elsewhere (e.g., arm, chest, leg, wrist etc.). In such embodiments, the band 102 may be configured to stretch around a given body part. Stated another way, the band 102 may be formed of a suitable material (e.g., an elastic material) to stretch around a given body part of the subject 106 for removable coupling to that body part. In some embodiments, the elastic band 102 may be formed of any purpose-suitable materials, such as elastic, latex, rubber, etc.

In some embodiments, the subject 106 may wear a plurality of iwEMS systems 100. For example, the subject 106 may wear an iwEMS system 100 on each arm or wear an iwEMS system 100 on each leg, or wear an iwEMS system 100 on a leg, an arm, and the head, or wear an iwEMS system 100 on the head, both legs, both arms, and the chest.

In the embodiment depicted in FIG. 5, the electromagnetic radiation transceivers 108 are equally spaced round the band 102 such that at least a portion of the electromagnetic radiation emitted by an electromagnetic transceiver 108 can reach another electromagnetic transceiver 108, e.g., via passage through a target tissue or otherwise. The arrangement of the electromagnetic transceivers 108 is not limited to that illustrated in FIG. 5, but other arrangements may also be utilized. For example, in one such arrangement, the electromagnetic transceivers 108 can be coupled to one half of the circumference of the band 102.

Figure 6:
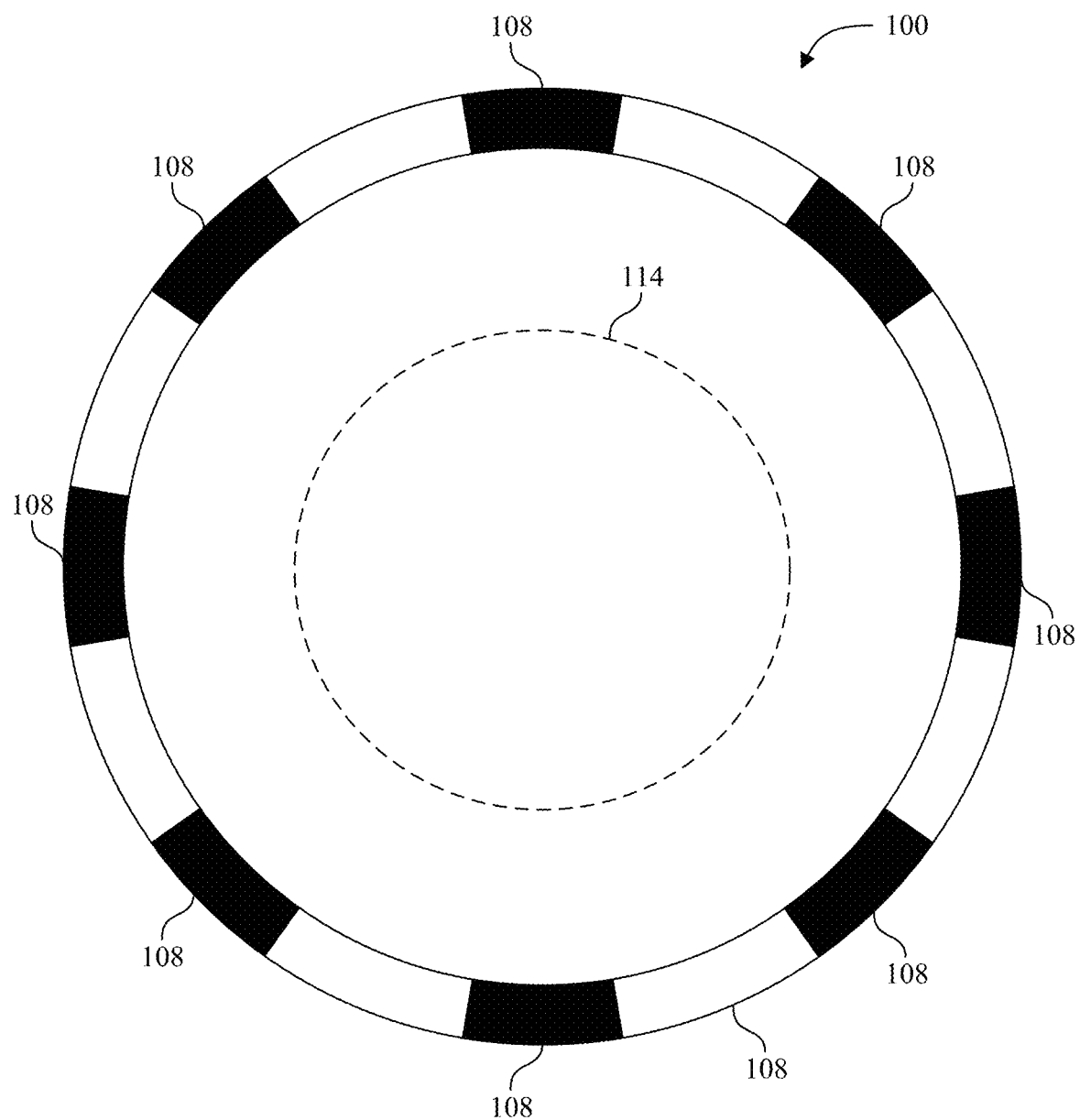
FIG. 6 diagrammatically illustrates an iwEMS device emitting electromagnetic radiation in accordance with an exemplary embodiment.

Briefly turning to FIG. 6, each of the electromagnetic radiation transceivers 108 may be configured to emit electromagnetic radiation and may be configured to detect electromagnetic radiation. The electromagnetic radiation transceivers 108 detect electromagnetic radiation transmitted through and/or reelected by tissue including the target tissue volume 114 and output signals indicative of the detected radiation. The frequency of the radiation emitted by the electromagnetic radiation sources can be selected so as to allow illumination of a whole volume of target tissues, including deep tissues. By way of example, when the iwEMS is deployed for interrogating brain tissue of an adult, the frequency of the emitted electromagnetic radiation may be between 0.01 and 3 GHz. In another example, when iwEMS 100 is deployed for interrogating leg or arm tissue, or when the iwEMS 100 is deployed for interrogating brain tissue of a newborn, the frequency of the emitted electromagnetic radiation may be between 0.01 and 10 GHz. In yet another example, when the iwEMS is deployed for interrogating chest tissue, the frequency of the emitted electromagnetic radiation may be between 0.01 and 2 GHz.

In other embodiments, the radiation emitted by an electromagnetic transceiver 108 may be detected by multiple electromagnetic transceivers 108, e.g., after the radiation passes through the irradiated tissue, which can contain the target tissue of interest. In some embodiments, each radiation transceiver may include scalar (just amplitude) or complex (e.g., amplitude and phase) radiofreqency detector and an Analog-to-Digital Converter (ADC) that produces a digital signal indicative of an analog signal generated by the detector in response to the detection of the incident radiation.

Figure 7:
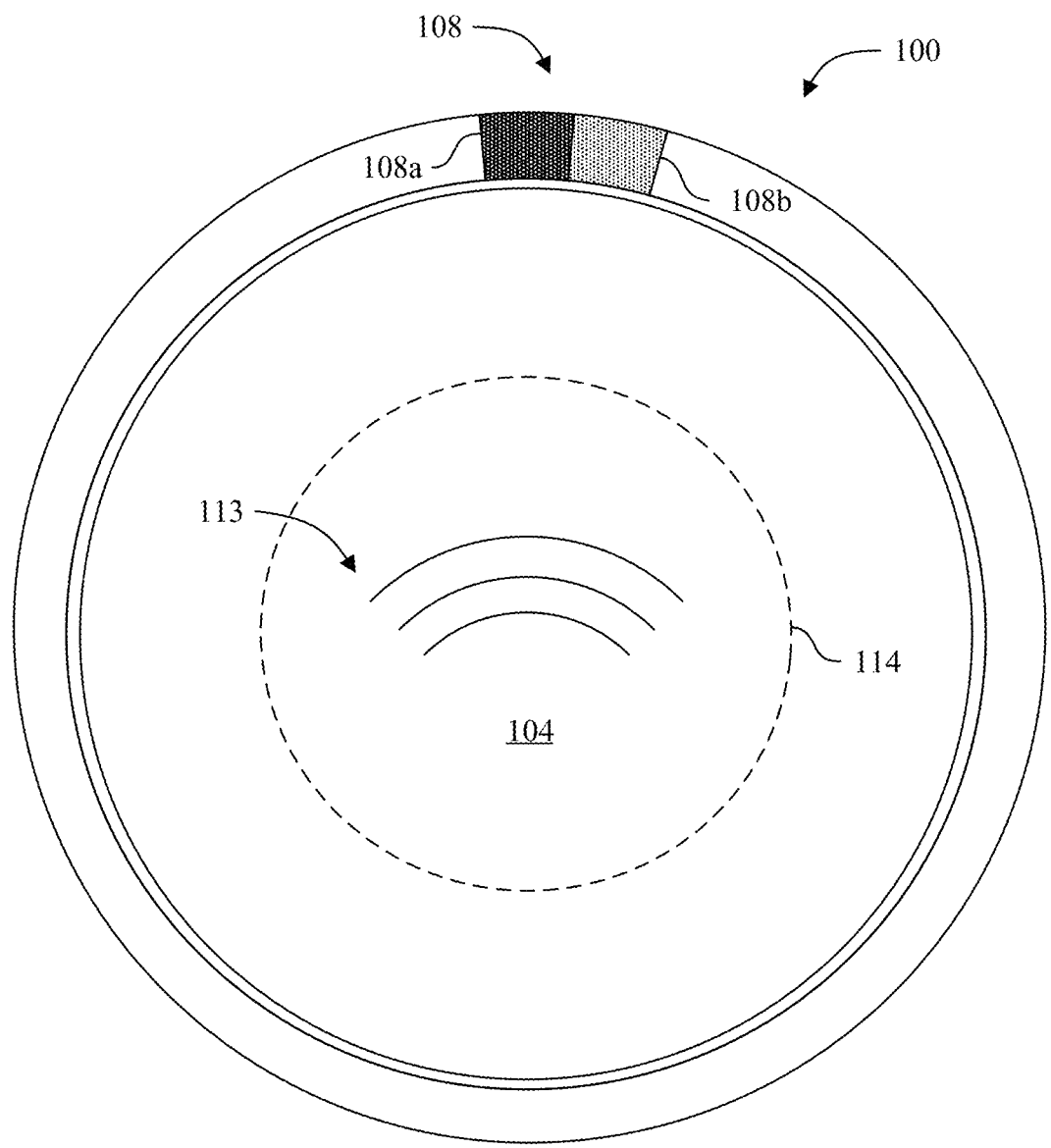
FIG. 7 diagrammatically illustrates an iwEMS with a single transceiver in accordance with an exemplary embodiment.

While the embodiments shown herein depict the iwEMS as including a plurality of electromagnetic transceivers 108, in other embodiments, as depicted in FIG. 7, the iwEMS 100 may include a single transceiver 108. In this embodiment, an electromagnetic radiation source component 108*a* emits electromagnetic radiation and an electromagnetic radiation detector component 108*b* of a transceiver 108 detects reflected radiation 113 that is reflected by biological material that is within a target tissue (e.g., biological material within the head 104 of the subject 106.

Figure 8:
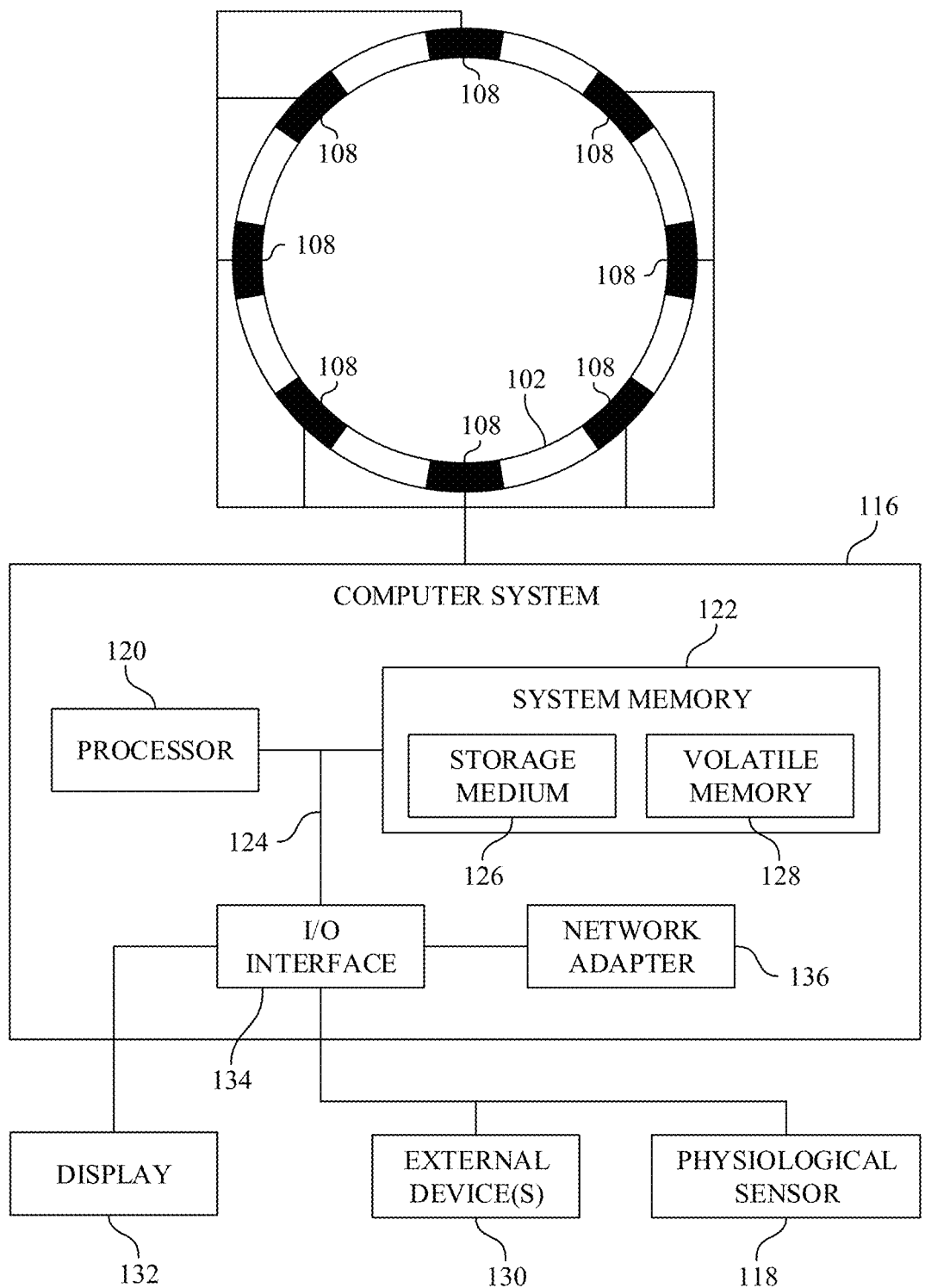
FIG. 8 diagrammatically illustrates an iwEMS device with a computer system in accordance with an exemplary embodiment.

Turning now to FIG. 8, a schematic diagram of the iwEMS 100 is shown in accordance with an exemplary embodiment. As shown in FIG. 8, the iwEMS 100 further includes a computer system 116 and a physiological sensor 118. In some embodiments, the physiological sensor 118 may be integrated into a wearable device (e.g., a watch). The computer system 116 is in wired or wireless communication with the transceivers 108 and the physiological sensor 118. In some embodiments the computer system 116 is in wireless communication with the transceivers 108 and the physiological sensor 118 when the computer system 116, the transceivers 108 and the physiological sensor 118 are connected to the same wireless network. In other embodiments, the computer system 116 is in wireless communication with the transceivers 108 and the physiological sensor 118 via a Bluetooth® connection. While FIG. 8 depicts the computer system 116 as separate from the electromagnetic radiation transceivers 108 and the band 102, in other embodiments, components of the computer system 116 (e.g., processor 120) may be integrated into the band 102 (e.g., as an application-specific integrated circuit (ASIC)).

The physiological sensor 118 measures one or more physiological parameters of the subject 106. The physiological sensor 118 includes, but is not limited to, a blood circulation sensor such as a heartbeat sensor or an ECG sensor or a blood pressure sensor. In one embodiment, the physiological sensor 118 measures a physiological parameter that exhibits a temporal periodicity related to natural variation of blood circulation through a target tissue. As the dielectric properties of the target tissue varies as a function of variations in its blood content (e.g., oxygenated blood content) within the target tissue, Applicant has discovered that information regarding oxygenation level of a target tissue, and in particular that of deep target tissue, may be acquired by illuminating the tissue via radiation having a frequency in a range of about 0.01 GHz to about 10 GHz, monitoring the radiation transmitted through and/or reflected from the tissue, and cross-correlating the monitored radiation with the temporal variations of the blood content in the tissue, The physiological sensor 118 may include an ADC that produces a digital signal indicative of the measured physiological parameter.

As used herein a computer system (or device) is any system/device capable of receiving, processing, and/or sending data. Examples of computer systems include, but are not limited to personal computers, servers, hand-held computing devices, tablets, smart phones, multiprocessor-based systems, mainframe computer systems, and distributed cloud computing environments that include any of the above systems and the like.

As shown in FIG. 8, the computer system 116 can include one or more processors or processing units 120, a system memory 122, and a bus 124 that allows communication between various components of the computer system 116 including the system memory 122 and the processor 120.

The system memory 122 includes a computer readable storage medium 126 and volatile memory 128 (e.g., Random Access Memory, cache, etc.). As used herein, a computer readable storage medium includes any media that is capable of storing computer readable program instructions and is accessible by a computer system. The computer readable storage medium 126 includes non-volatile and non-transitory storage media (e.g., flash memory, read only memory (ROM), hard disk drives, etc.). Computer readable program instructions as described herein include program modules (e.g., routines, programs, objects, components, logic, data structures, etc.) that are executable by a processor. Furthermore, computer readable program instructions, when executed by a processor, can direct a computer system (e.g., the computer system 116) to function in a particular manner such that a computer readable storage medium (e.g., the computer readable storage medium 126) comprises an article of manufacture. Specifically, when the computer readable program instructions stored in the computer readable storage medium 126 are executed by the processor 120 create means for implementing the functions specified in the method 1000 depicted in FIG. 10.

The bus 124 may be one or more of any type of bus structure capable of transmitting data between components of the computer system 116 (e.g., a memory bus, a memory controller, a peripheral bus, an accelerated graphics port, etc.).

In some embodiments, as depicted in FIG. 8, the computer system 116 may include one or more external devices 130 and a display 132. As used herein, an external device includes any device that allows a user to interact with a computer system (e.g., mouse, keyboard, touch screen, etc.). An external device 130 and the display 132 in communication with the processor 120 and the system memory 122 via an Input/Output (I/O) interface 134.

The display 132 may display a graphical user interface (GUI) that may include a plurality of selectable icons and/or editable fields. A user may use an external device 130 (e.g., a mouse) to select one or more icons and/or edit one or more editable fields. Selecting an icon and/or editing a field may cause the processor 120 to execute computer readable program instructions stored in the computer readable storage medium 126. In one example, a user may use an external device 130 to interact with the computer system 116 and cause the processor 120 to execute computer readable program instructions relating to the method 1000 depicted in FIG. 10.

The computer system 116 may further include a network adapter 136 which allows the computer system 116 to communicate with one or more other computer systems/devices via one or more networks (e.g., a local area network (LAN), a wide area network (WAN), a public network (the Internet), etc.).

The computer system 116 is in wired or wireless communication with each of the transceivers 108 and the physiological sensor 118. The computer system 116 may be utilized to control one or more of the transceivers 108 and the physiological sensor 118.

Figure 9:
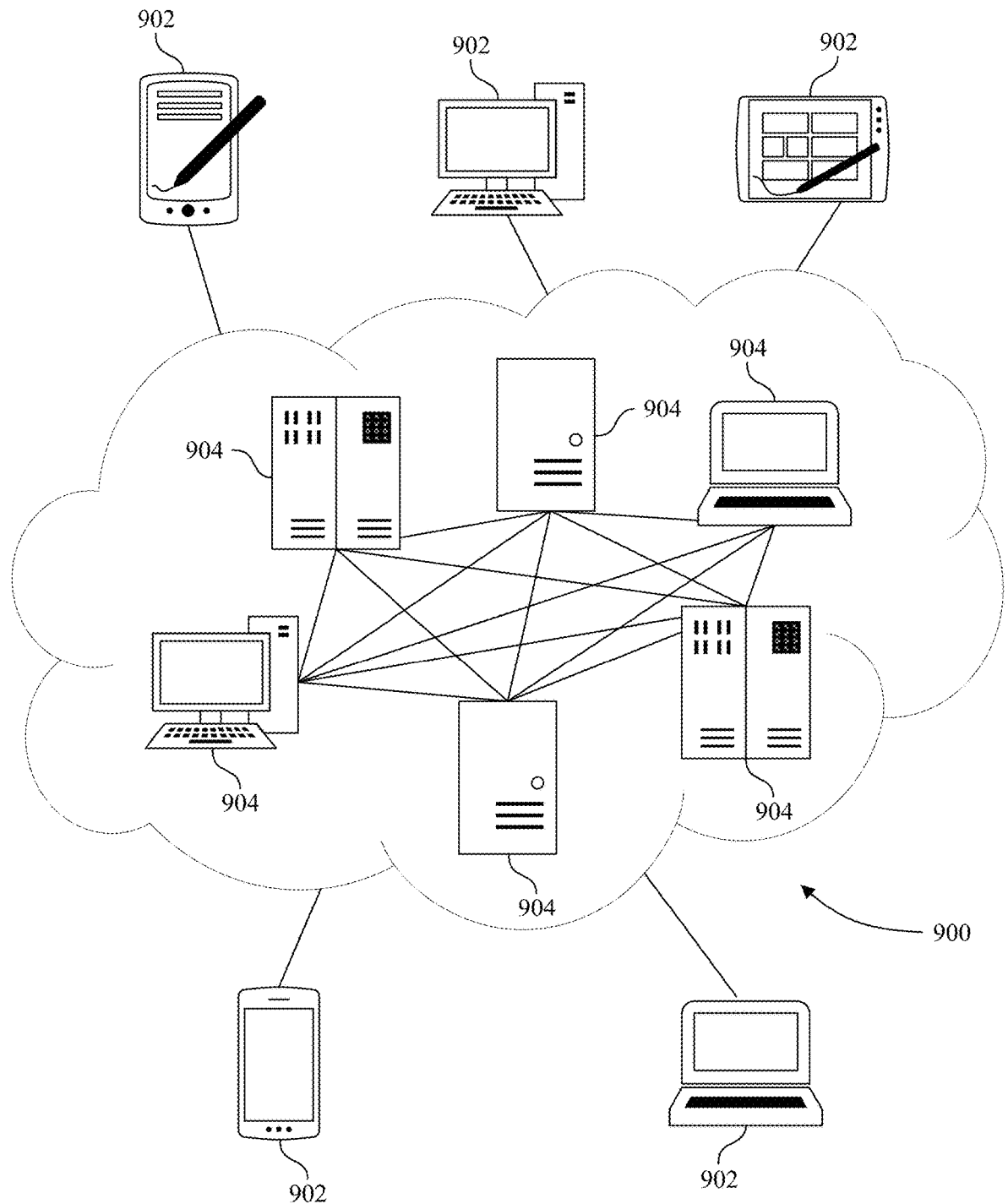
FIG. 9 depicts a cloud computing environment in accordance with an exemplary embodiment.

Referring now to FIG. 9 a cloud computing environment 900 connected to one or more user computer systems 902 is depicted in accordance with an exemplary embodiment. In one embodiment, a computer system 902 is the computer system 116. The cloud computing environment 900 provides network access to shared computing resources (e.g., storage, memory, applications, virtual machines, etc.) to the one or more user computer systems 902. As depicted in FIG. 9, the cloud computing environment 900 includes one or more interconnected nodes 904. Each node may be a computer system or device with local processing and storage capabilities. The nodes 904 may be grouped and in communication with one another via one or more networks. This allows the cloud computing environment 900 to offer software services to the one or more user computer systems 902 and as such, a user computer system 902 does not need to maintain resources on a locally.

Figure 10:
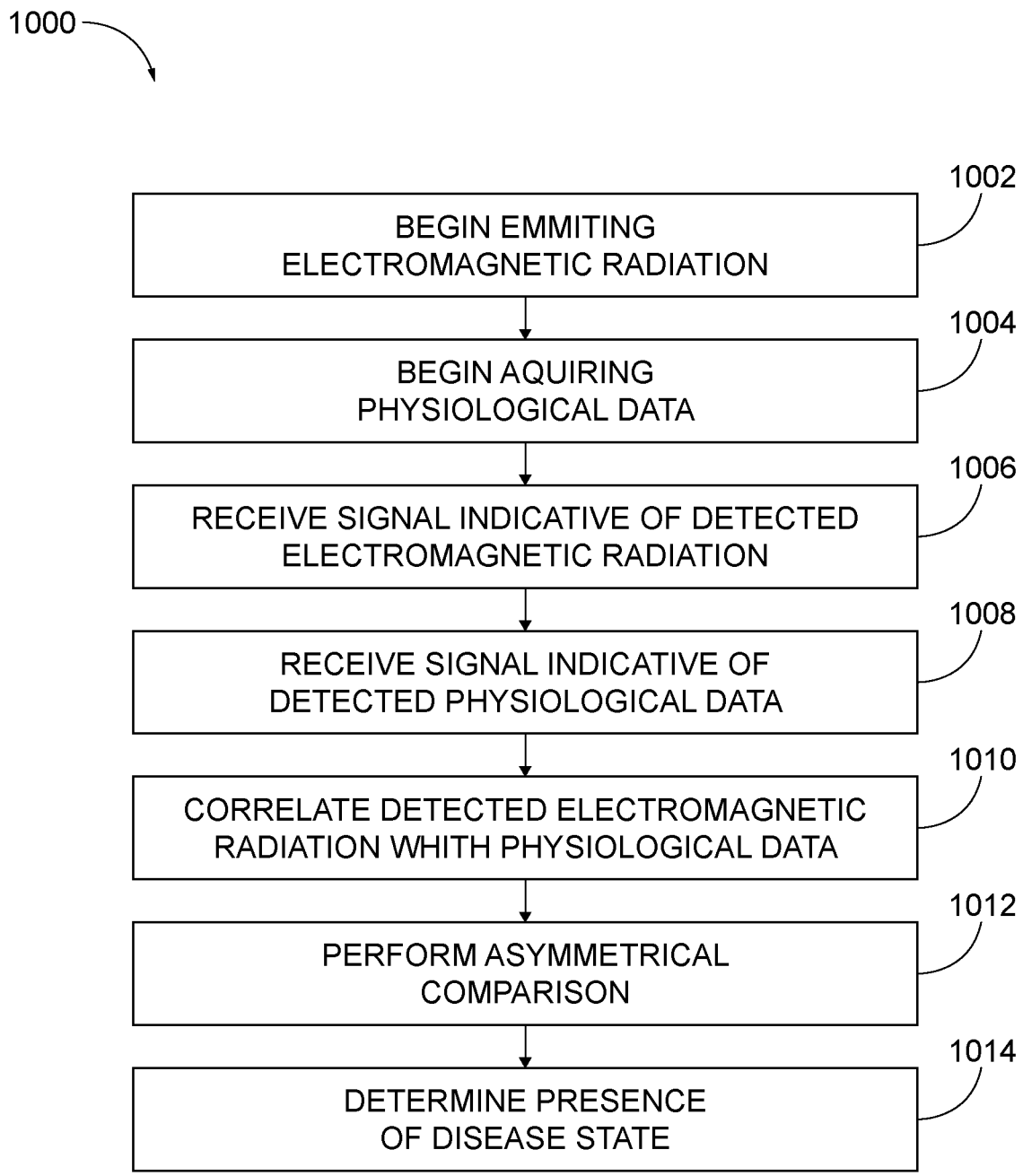
FIG. 10 depicts a method for electromagnetically sensing biological tissues for non-invasively assessing blood content, oxygenation status, and viability of biological tissues in accordance with an exemplary embodiment.

In one embodiment, a node 904 includes the system memory 122 and as such, includes the computer readable program instructions for carrying the method 1000 of FIG. 10. In this embodiment, a user of a user computer system 902 that is connected the cloud computing environment 900 may cause a node 904 to execute the computer readable program instructions to carry out the method 1000.

Referring now to FIG. 10, a method 1000 for electromagnetically sensing biological tissues for non-invasively assessing a blood content, oxygenation status, and viability of biological tissue is shown in accordance with an exemplary embodiment. As previously discussed herein, the steps 1002-1014 of the method 1000 may be stored as computer readable program instructions in a computer readable storage medium (e.g., the computer readable storage medium 126). A digital processor that is configured according to an aspect of the present disclosure (hereinafter "a configured processor") executes the computer readable program instructions for performing the method 1000. In one embodiment, the configured processor is the processor 120.

At 1002, the configured processor sends a control signal to transceiver 108 to cause the transceiver to begin emitting electromagnetic radiation. In response to receiving the signal, the transceiver 108 emits the electromagnetic radiation 112 as previously discussed herein.

At 1004, the configured processor sends a control signal to the physiological sensor 118 to cause the sensor to begin acquiring physiological data. In response to receiving the control signal to begin acquiring physiological data, the physiological sensor 118 begins acquiring physiological data relating to a physiological parameter as previously discussed herein. In one embodiment, the configured processor sends a control signal to one or more transceivers to cause the transceivers to emit and detect electromagnetic radiation and sends a control signal to a physiological sensor to begin acquiring physiological data. In some cases, the timing of the control signals can be configured such that the detected radiation data and the physiological data are collected substantially simultaneously. As such, a transceiver 108 and a physiological sensor 118 may synchronously record detected radiation and physiological data.

At 1006, the configured processor receives a signal indicative of detected electromagnetic radiation as previously discussed herein. In some embodiments, at 1006, the configured processor further quantifies one or more aspects of the received radiation signal (e.g., a ratio of the intensity (in scalar cases) together with phase (in complex cases) of the detected radiation relative to the intensity (in scalar cases) together with phase (in complex cases) of the illuminating radiation) indicative of the interaction of the electromagnetic radiation with the illuminated tissue, such as absorption and/or scattering, diffraction and interference of the radiation as it passes through the illuminated tissue.

At 1008, the configured processor receives one or more physiological signals indicative of the detected physiological data from the physiological sensor 118.

At 1010, the processor is configured to determine a cross-correlation function of the detected radiation signals and the physiological data to compute contribution of the target tissue to variations observed in the detected radiation signals. More specifically, the configured processor calculates the cross correlation function of the received and further digitized signal(s) indicative of detected electromagnetic radiation $\Sigma_{i=1}^{N} E_i$ with the received and further digitized signal(s) indicative of the detected physiological data, $\Sigma_{i=1}^{N} F_i$. The cross-correlation function ($R_k$), between two series of digitized signals is calculated according to:

$$R_k = \sum_{i=1+k}^{M+k} E_i \times (E_i - E_{mean}) \times$$

$$(F_i - F_{mean}) \bigg/ \left( \sqrt{\sum_{i=1+k}^{M+k} (E_i - E_{mean})^2} \times \sqrt{\sum_{i=1+k}^{M+k} (F_i - F_{mean})^2} \right)$$

where M is the sample size, to be chosen by trial method (for example, the number of digitized signals over one cycle of circulation or a portion of cardiac cycle which corresponds to the duration of a systola) M<N; k varies from 0 to (N−M); index "mean" corresponds to an averaged signal over M samples, starting from 1+k and ending at M+k; $E_i$ is an $i^{th}$ reading of digitized electromagnetic radiation signal (for example: an amplitude or a phase); $E_{mean}$ is a mean of the electromagnetic signals in the sample size; $F_i$ is an $i^{th}$ reading of digitized physiological signal; and $F_{mean}$ is a mean of the physiological data signals in the sample size. By way of example and without limitation, the sample size M can be in a range of about 10 to about 10000. When the emitted radiation includes radiation across multiple frequencies, the configured processor may utilize the above equation to determine a cross-correlation function for each of the plurality of frequencies within the band ("frequency-dependent cross-correlation functions"). The above equation may be applied to aspects of two signals in order to determine a relatedness between the aspects. For example, the above may provide a cross-correlation between phase of detected electromagnetic radiation and a given physiological signal, may provide a cross-correlation between amplitudes of detected electromagnetic radiation and a given physiological signal. As such, values for $E_i$ and $F_i$ correspond to aspects of a given the electromagnetic radiation signal and a given physiological signal (e.g., a amplitude, or a phase of the signal) and $E_{mean}$ and $F_{mean}$ correspond to similar averaged aspects electromagnetic radiation signal and the physiological signal within the set (e.g., an average amplitude, an averaged phase, etc.). Accordingly, the configured processor can be said to determine a cross correlation function of phase, a cross correlation of amplitude etc. In other embodiments a systole vs. diastola coefficient $$\left( SvD = \frac{R^{sys}}{R^{dia}} \right)$$

may be introduced into further analysis of the cross-correlation function. This coefficient is introduced to compare cross-correlation coefficients within a same cardiac cycle, but is obtained at different phases of circulation (systolic vs. diastolic) at different phases of blood content in the tissue.

Figure 11:
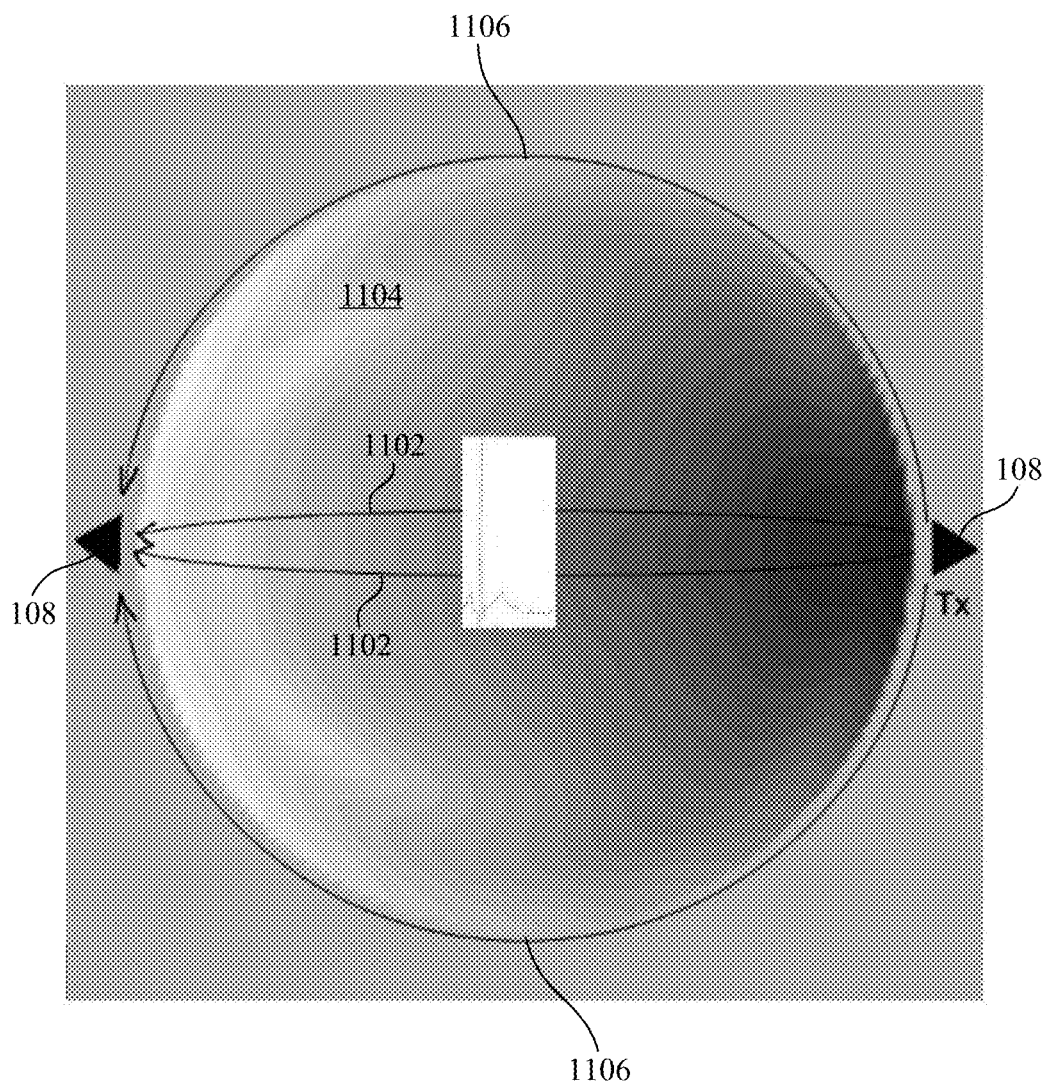
FIG. 11 diagrammatically illustrates pathways of electromagnetic radiation through and around a biological tissue in accordance with an exemplary embodiment.
Figure 12:
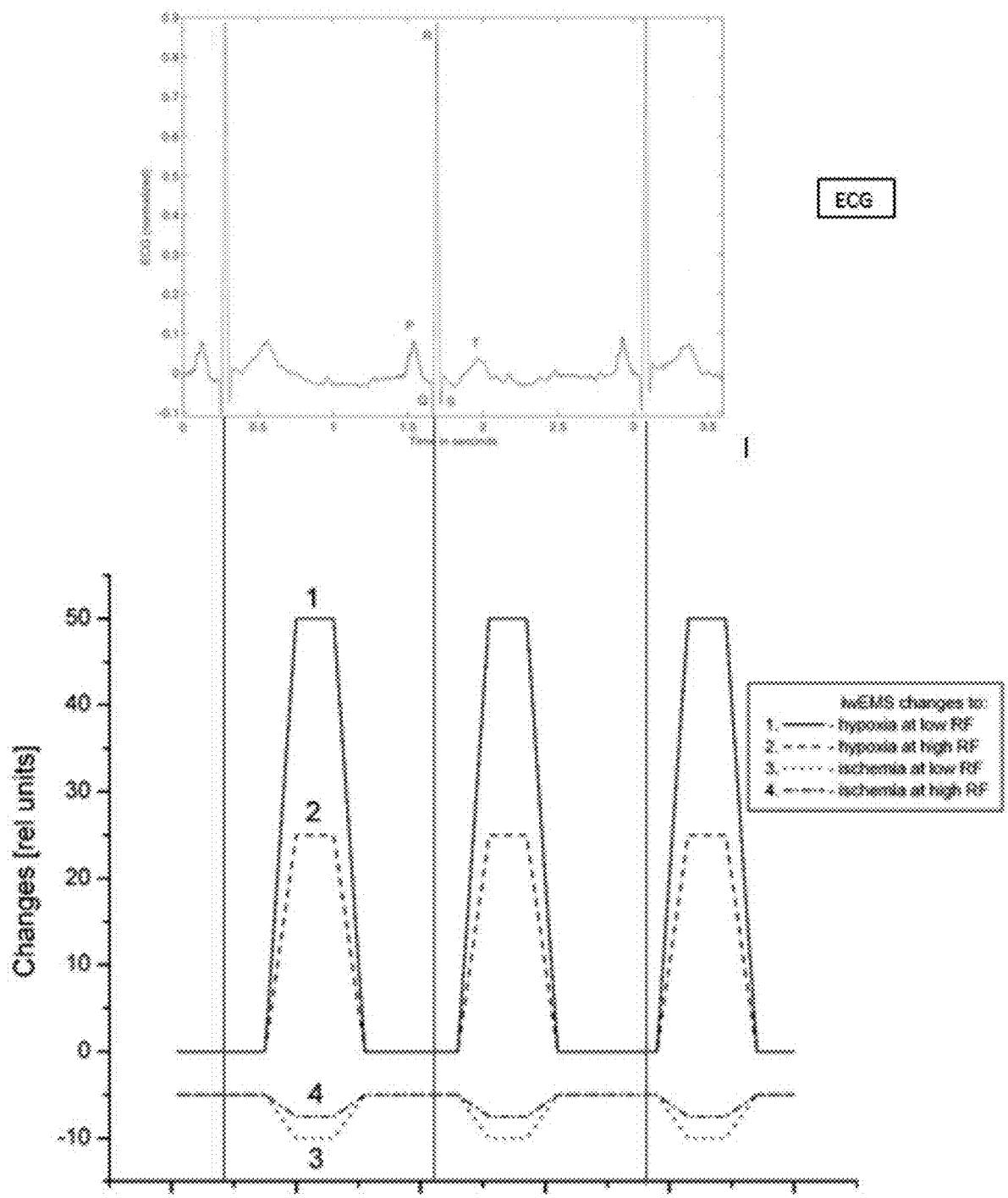
FIG. 12 is a graphical representation of projected hypoxia/ischemia changes in recorded iwEMS signals linked to cardiac cycle in accordance with an exemplary embodiment.

Briefly turning to FIG. 11, in an optimal situation, the electromagnetic radiation emitted from an a transceiver 108 travels along path 1102 through a biological tissue 1104 to another transceiver 108 (hereinafter referred to as "informative electromagnetic radiation"), which generates detected radiation signals. In practice, a portion of the emitted electromagnetic radiation may reach a transceiver without passing through the target tissue by travelling along a path 1106 to another transceiver (hereinafter referred to as "noninformative electromagnetic radiation").

As such, a transceiver 108 detects both informative electromagnetic radiation (radiation that has been attenuated and interfered by a biological tissue) and noninformative electromagnetic radiation (passing around a target), which may be larger in amplitude. However, the only informative signal is "coded" by physiological activity within interrogated biological tissue, for example blood circulation. By cross correlating the received signal indicative of detected electromagnetic radiation with the received signal indicative of detected physiological data, only the informative portion of detected electromagnetic radiation may be further analyzed. For example, the configured processor may determine only signals indicative of detected electromagnetic radiation received within a given time threshold with respect to signals indicative of a physiological parameter (e.g., a cardiac cycle) are indicative of informative electromagnetic radiation and may discard the rest of the signals may be identified as being noninformative. In one embodiment at 1010, the configured processor computes a cross-correlation function of amplitude between an amplitude of the at least one detected radiation signal and the at least one physiological signal. In another embodiment at 1010, the configured processor computes a cross-correlation function of phase between a phase of the at least one detected radiation signal and the at least one physiological signal. The configured processor determines a signal is informative when a cross correlation function of phase and/or amplitude is within a given threshold.

Figure 3:
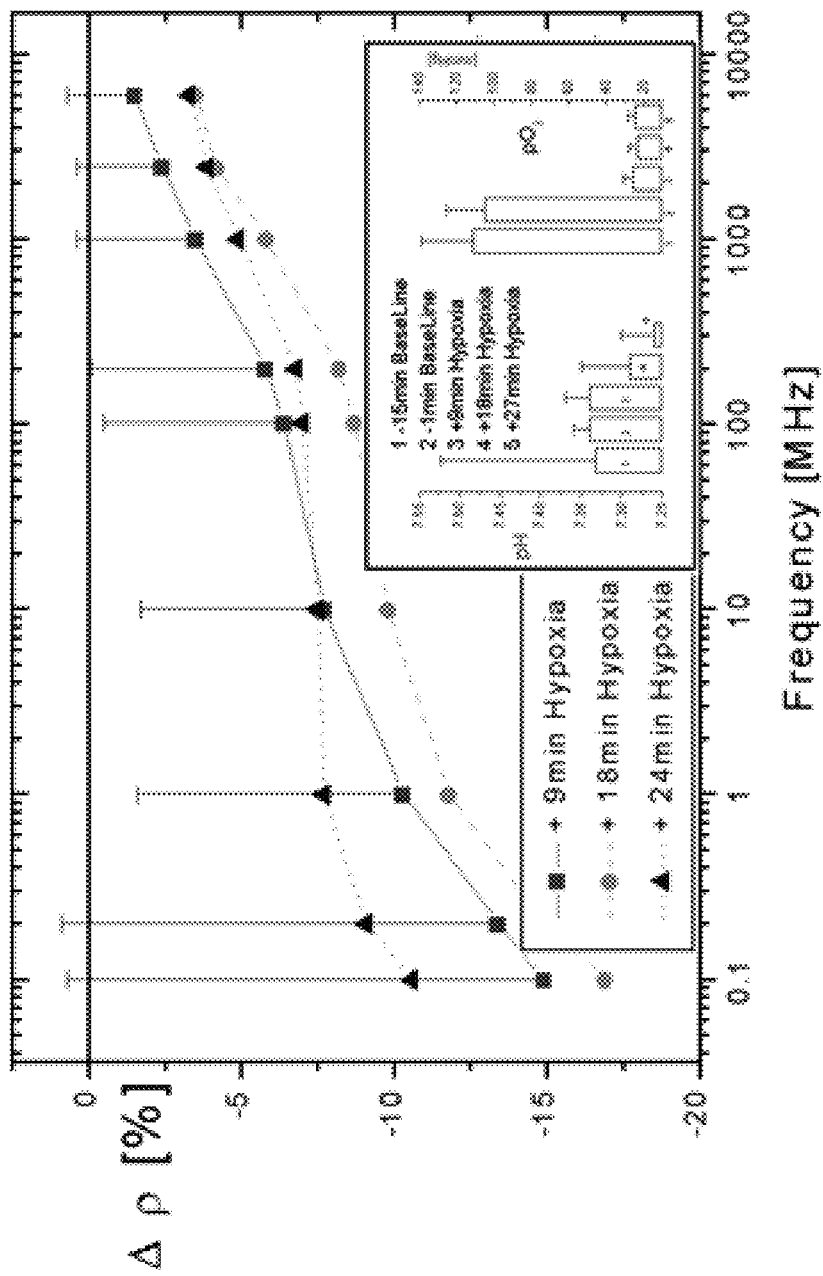
FIG. 3 is a graphical representation of spectral and temporal changes in resistance of myocardial tissue during 10% hypoxia.

As depicted in FIG. 3, when the tissue (or at least a portion thereof) in the target tissue becomes hypoxic, its dielectric properties change in such a way that causes more attenuation of electromagnetic radiation with expected negligible effect on phase. The changes are more pronounced at low frequencies (e.g., at a frequency less than about 1 GHz). Therefore, it is expected that signals indicative of detected electromagnetic radiation will change with more pronounced effect at lower frequencies. As modified cross-correlation function is proportional to the value of detected electromagnetic radiation Et (either amplitude or phase or both), it is also expected that as a tissue becomes more hypoxic, there is a higher cross-correlation functions of the amplitude of detected electromagnetic radiation with the signal indicative of the detected physiological data (e.g., ECG data) with an inverse proportion to the frequency. It is expected that such hypoxic tissue changes cause a negligible effect in phase of detected electromagnetic signal. In non-tissue damaging cases of hypoxia, a dynamic cross correlation value of the signals indicative of the detected radiation and the signals indicative of the detected physiological data returns to a baseline value after a given time interval. It is also expected, that when tissue becomes hypoxic the SvD coefficient will change, as there is a different amount of hypoxic blood in the tissue.

Figure 4A:
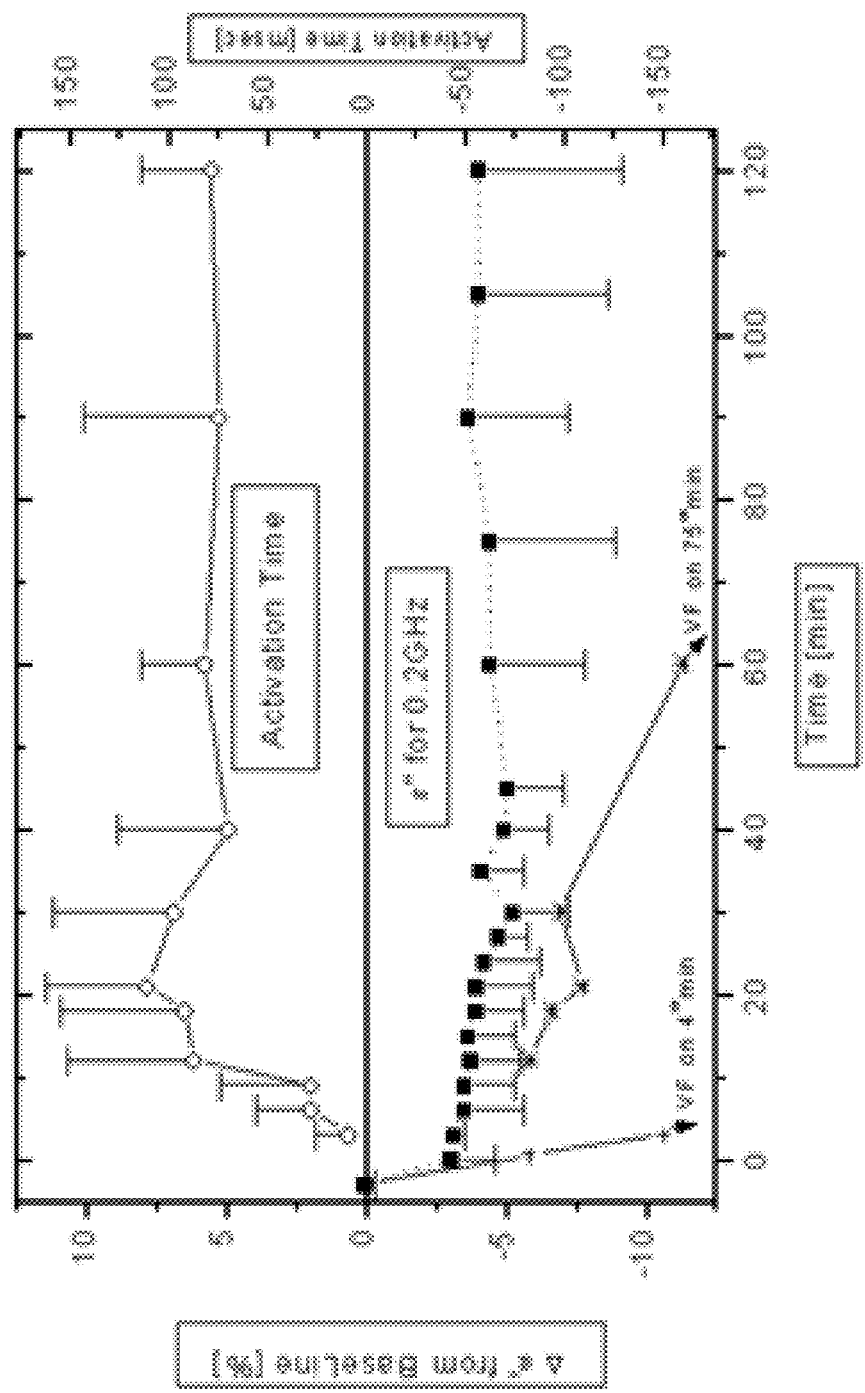
FIG. 4A is a graphical representation of changes in imaginary part of dielectric properties of myocardial tissue at 0.2 GHz following total occlusion of left anterior descending (LAD) artery.
Figure 4C:
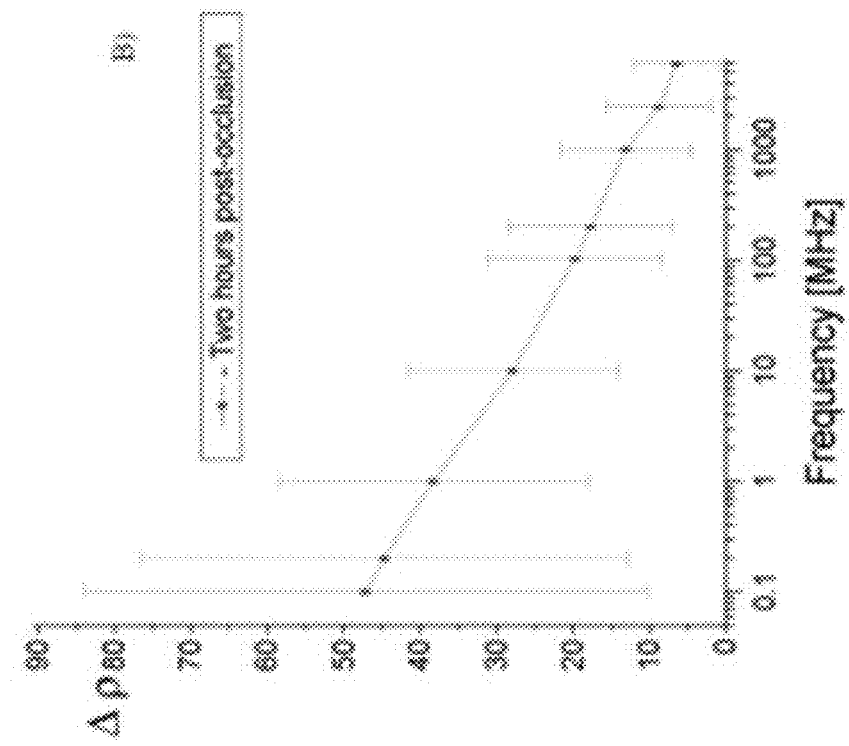
FIG. 4C is a graphical representation of spectral changes in resistance p of myocardial tissue during 2-hr acute ischemia.
Figure 4B:
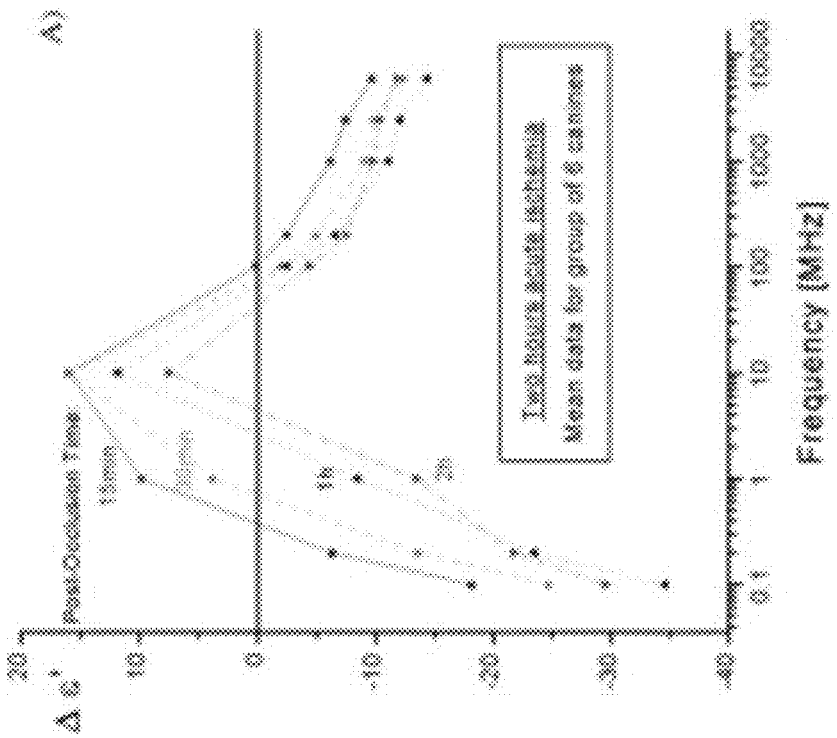
FIG. 4B is a graphical representation of spectral changes in dielectric permittivity (real part) ε' of myocardial tissue during 2-hr acute ischemia.

As depicted in FIGS. 4A, 4B, and 4C, when there is an occurrence of tissue ischemia leading to an ischemic tissue injury and damage, the dielectric properties of a tissue change in such a way such that there is less attenuation of the electromagnetic radiation passing through the target tissue with expected frequency and time dependent effect on phase. The changes in amplitude are more pronounced at low frequencies. It is expected that signals indicative of detected electromagnetic radiation signals will change (or change a sign), causing changes in cross-correlation functions with signals indicative of detected physiological data (e.g., ECG) that are opposite to changes in amplitude in hypoxia cases. It is also expected that ischemia causes frequency and time dependent changes in cross-correlation in phase, that are not observed during hypoxia. In ischemic tissue damage, value of signals indicative of detected electromagnetic radiation will fall off from a baseline value.

Returning to FIG. 10, at 1012, in some embodiments, the configured processor performs an asymmetrical comparison by comparing information related to functional and/or pathological conditions of biological tissues within a target volume 114 of one or more iwEMS 100 (e.g., biological tissue within a target volume 114 of an iwEMS 100 worn on a right arm vs. biological tissue within a target volume 114 of an iwEMS 100 worn on a left arm, biological tissue within a target volume 114 of an iwEMS 100 worn on a right leg vs. biological tissue within a target volume 114 of an iwEMS 100 worn on a left leg, biological tissue within a target volume 114 of an iwEMS 100 corresponding to a right hemisphere of the brain vs. biological tissue within a target volume 114 corresponding to a left hemisphere of the brain, etc.). Furthermore, the asymmetrical comparison may include comparing prior data stored in a computer readable storage medium (e.g., the computer readable storage medium 126 or a computer readable storage medium of a node 904 of the cloud computing environment 900). There are limited cases when a pathology occurs simultaneously in, for example both extremities or both hemispheres in the brain. Therefore, it is very useful to compare dynamically data from a target area with suspected pathology with the same type of data from normal area or with "normal" data previously acquired from target area and stored.

At 1014, the configured processor determines a physiological/pathological condition (e.g., hypoxia, ischemia, oxygen content, tissue malignancy (e.g., tissue malignancy that results in an increase in tissue metabolic rate that is higher than normal tissue blood content), tissue viability, blood content, etc.) of a subject based on i) cross-correlation analysis in 1010 (as described above) and/or optionally ii) the asymmetrical comparison at 1012. In some embodiments, the configured processor determines a physiological/pathological condition based only on i) cross-correlation analysis of informative signals (as described above) and/or ii) the asymmetrical comparison of informative signals. Furthermore, at 1014, the configured processor causes the display 132 to display a notification indicating the determined physiological/pathological condition. The configured processor may determine the physiological/pathological condition when a difference between cross-correlation functions exceeds a threshold. For example, at 1012, the configured processor may compare a cross-correlation coefficient corresponding to a right hemisphere of the brain with a cross-correlation coefficient for a left hemisphere of the brain. When the two differ by a threshold amount, the configured processor may determine the physiological/pathological condition. In another example, at 1012, the configured processor may compare a cross-correlation function of the chest with a reference cross-correlation of the chest wherein the chest is in a normal state. In this example, when the two differ by a threshold amount, e.g., by greater than about two standard deviations, the configured processor may determine the physiological/pathological condition.

The configured processor may perform the above steps for a prolonged period (e.g., across two or more cardiac cycles). As such, the configured processor may be said to continuously determine cross-correlation functions in order to monitor a subject's health and may continuously determine the physiological/pathological condition of the subject wearing the iwEMS 100.

In one embodiment, the configured processor determines a hypoxic condition when a cross-correlation function of an amplitude varies by a threshold amount from a second cross-correlation function of an amplitude (e.g., a cross-correlation function that corresponds to a normal physiological condition, a cross-correlation function that corresponds to a related tissue, etc.) and when the cross-correlation function of a phase does not vary by a threshold amount from the second cross-correlation function of a phase over a predetermined time and/or frequency. The threshold amount may be chosen by a trial method, as an example it can be equal to the value of two standard deviation of cross-correlation function at a normal physiological conditions.

In another embodiment, the configured processor determines an ischemic condition when a cross-correlation function of an amplitude varies in an opposite direction with respect to a change in a cross-correlation function of an amplitude associated with hypoxia as well as when a temporal and frequency-dependent changes occur in a cross-correlation function of a phase. Furthermore, when the configured processor determines multiple frequency-dependent cross-correlation functions, the configured processor may perform the above comparison(s) for each frequency-dependent cross-correlation function when determining physiological/pathological condition.

The configured processor may employ a trained neural network when determining the presence or absence of the disease state. The neural network may have been previously trained using previously obtained interference characteristics of several portions of human body as well as other physiological parameters obtained by physiological sensors 118. Stated another way, the configured processor may employ artificial intelligence capabilities when determining the presence or absence of the disease state.

As previously discussed, the above may be implemented by way of computer readable instructions, encoded or embedded on computer readable storage medium (which excludes transitory medium), which, when executed by a processor(s), cause the processor(s) to carry out the methods of the present disclosure.

While the disclosure describes the drawings and foregoing description, such illustration and description are to be considered illustrative or exemplary and not restrictive; embodiments of the present disclosure are not limited to the disclosed embodiments. Other variations to the disclosed embodiments can be understood and effected by those skilled in the art in practicing embodiments of the present disclosure, from a study of the drawings, the disclosure, and the appended claims.

In the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

What is claimed is:

1. A system for non-invasive in-vivo assessment of at least one physiological condition of tissue, comprising:
   at least one physiological sensor configured to monitor at least one circulatory physiological parameter of a subject and to generate at least one physiological signal indicative of the monitored physiological parameter, wherein the physiological parameter is indicative of temporal variations of blood circulation within a tissue portion containing a target tissue of interest;
   at least one radiation source configured to irradiate the tissue portion with electromagnetic radiation;
   at least one radiation detector configured to detect at least a portion of the irradiating radiation transmitted through or reflected by the tissue portion and to generate at least one detected radiation signal, wherein the radiation source and the radiation detector are configured, respectively, to generate and detect electromagnetic radiation frequencies in a range of about 0.01 GHz to about 10 GHz; and a digital processor configured to receive the physiological and detected radiation signals and process the signals to derive information regarding the at least one physiological condition within the target tissue, wherein the digital processor is configured to utilize the following relation to compute a cross-correlation function of amplitude between an amplitude of the at least one detected radiation signal and an amplitude of the at least one physiological signal:

$$\sum\nolimits_{i=1+k}^{M+k} E_i \times (E_i - E_{mean}) \times$$

$$(F_i - F_{mean}) \Big/ \left( \sqrt{\sum\nolimits_{i=1+k}^{M+k} (E_i - E_{mean})^2} \times \sqrt{\sum\nolimits_{i=1+k}^{M+k} (F_i - F_{mean})^2} \right)$$

wherein, Ei denotes an $i^{th}$ reading of digitized electromagnetic radiation signal corresponding to amplitude or phase, Emean denotes a mean of the electromagnetic signals in the sample size; Fi denotes an $i^{th}$ reading of digitized physiological data signal and Fmean denotes a mean of the physiological data signals in the sample size.

2. The system of claim 1, wherein the at least one radiation source and the at least one detector are incorporated in a single transceiver.

3. The system of claim 1, wherein the digital processor is further configured to compute a cross-correlation function of phase between a phase of the at least one detected radiation signal and a phase of the at least one physiological signal and is configured to utilize the cross correlation functions of amplitude or phase to determine whether the at least one detected radiation signal is an informative or a non-informative signal.

4. The system of claim 1, wherein the physiological condition comprises at least one of a blood content, an oxygen content, tissue ischemia, tissue hypoxia, a tissue malignancy, and tissue viability, wherein the malignancy comprises a type of malignancy resulting in an increase in tissue metabolic rate and thus a higher than normal tissue blood content.

5. The system of claim 1, wherein the circulatory physiological parameter comprises at least one of ECG and cardiac pulse.

6. The system of claim 1, wherein the digital processor is configured to compare the cross-correlation function with a reference cross-correlation function to derive the information regarding the at least one physiological condition with the target tissue.

7. The system of claim 1, wherein the at least the one radiation source is configured to generate radiation at a plurality of frequencies in the frequency range of about 0.01 GHz to about 10 GHz for irradiating the tissue at the plurality of frequencies.

8. The system of claim 7, wherein the at least one detector is configured to detect radiation transmitted or reflected by the irradiated tissue at the plurality of frequencies, and to generate at least one detected radiation signal at each of the frequencies, the digital processor is further configured to determine a cross-correlation function associated with each of the plurality of frequencies, and wherein the digital processor is configured to compare the frequency-dependent cross correlation functions to determine the at least one physiological condition.

9. The system of claim 1, wherein the system is incorporated into a wearable device including a flexible band that can be worn around a subject's head for in-vivo assessment of brain tissue.

10. The system of claim 9, wherein the at least one radiation source comprises two or more radiation sources and said at least one detector comprises two or more detectors, wherein the radiation sources and the detectors are coupled to the flexible band.

11. The system of claim 10, wherein the two or more radiation sources and the two or more radiation detectors are distributed around the flexible band such that each detector detects electromagnetic radiation transmitted through and/or reflected by the brain tissue in response to irradiation of the brain tissue by radiation generated by at least one of the two or more radiation sources and outputs signals indicative of the detected radiation.

12. A system for non-invasive in-vivo assessment of at least one physiological condition of tissue, comprising:

at least one physiological sensor configured to monitor at least one circulatory physiological parameter of a subject and to generate at least one physiological signal indicative of the monitored physiological parameter, wherein the physiological parameter is indicative of temporal variations of blood circulation within a tissue portion containing a target tissue of interest;

at least one radiation source configured to irradiate the tissue portion with electromagnetic radiation;

at least one radiation detector configured to detect at least a portion of the irradiating radiation transmitted through or reflected by the tissue portion and to generate at least one detected radiation signal, wherein the radiation source and the radiation detector are configured, respectively, to generate and detect electromagnetic radiation frequencies in a range of about 0.01 GHz to about 10 GHz; and a digital processor configured to receive the physiological and detected radiation signals and process the signals to derive information regarding the at least one physiological condition within the target tissue, wherein the digital processor is configured to compute a cross-correlation function of amplitude between an amplitude of the at least one detected radiation signal and an amplitude of the at least one physiological signal, wherein the at least one radiation source is configured to generate radiation at a plurality of frequencies in the frequency range of about 0.01 GHz to about 10 GHz for irradiating the tissue at the plurality of frequencies, wherein the at least one detector is configured to detect radiation transmitted or reflected by the irradiated tissue at the plurality of frequencies to generate at least one detected radiation signal at each of the frequencies, the digital processor is further configured to determine a cross-correlation function associated with each of the plurality of frequencies, and wherein the digital processor is configured to compare the frequency-dependent cross correlation functions to determine the at least one physiological condition, wherein the digital processor is configured to identify an ischemic condition of the target tissue based on detecting a change in the cross-correlation function of amplitude in a direction opposite to a direction of change exhibited by the cross-correlation function of amplitude in a hypoxic tissue condition as well as detecting a temporal and frequency-dependent change in the cross-correlation function of phase.

13. A method for non-invasive in-vivo assessment of at least one physiological condition of tissue, comprising:
monitoring at least one circulatory physiological parameter of the subject to generate one or more physiological signals, wherein the physiological parameter is indicative of temporal variations in blood circulation within a tissue portion containing a target tissue of interest,
irradiating the tissue portion with electromagnetic radiation having a frequency in a range of about 0.01 GHz to about 10 GHZ,
detecting at least a portion of the radiation transmitted or reflected by the irradiated tissue to generate one or more detected radiation signals,
synchronizing the detected radiation signals with the physiological signals, and
processing the synchronized detected radiation signals and the physiological signals to obtain information regarding a physiological condition within the target tissue,
wherein the processing step comprises computing a cross correlation function of amplitude between an amplitude of the at least one of the detected radiation signals and an amplitude of the at least one of the physiological signals,
wherein cross-correlation of the radiation detection signals and the physiological signals is performed via the following relation:

$$\sum_{i=1+k}^{M+k} E_i \times (E_i - E_{mean}) \times (F_i - F_{mean}) / \left( \sqrt{\sum_{i=1+k}^{M+k} (E_i - E_{mean})^2} \times \sqrt{\sum_{i=1+k}^{M+k} (F_i - F_{mean})^2} \right)$$

wherein, $E_i$ denotes an $i^{th}$ reading of digitized electromagnetic radiation signal corresponding to amplitude or phase, $E_{mean}$ denotes a mean of the electromagnetic signals in the sample size; $F_i$ denotes an ith reading of digitized physiological data signal and $F_{mean}$ denotes a mean of the physiological data signals in the sample size.

14. The method of claim 13, wherein the processing step further comprises computing a cross correlation function of phase between a phase of the at least one of the detected radiation signals and a phase of the at least one of the physiological signals and the method further comprises utilizing any of the amplitude or phase correlation functions to distinguish between informative and non-informative detected radiation signals.

15. The method of claim 13, wherein the physiological condition comprises at least one of blood content, oxygen content, tissue ischemia, a tissue malignancy, and tissue viability, wherein the tissue malignancy comprises any of malignant tissue with increased metabolism, resulting in higher blood content.

16. The method of claim 13, wherein the circulatory physiological parameter comprises at least one of ECG or cardiac pulse.

17. The method of claim 13, further comprising:
comparing the cross-correlation function of phase or amplitude with a reference cross-correlation function to obtain the information about the at least one physiological condition of the target tissue; and
comparing the cross-correlation function to determine the physiological condition of the tissue.

18. The method of claim 13, wherein the step of irradiating the tissue comprises irradiating the tissue at two or more frequencies in the frequency range of about 0.01 GHz to about 10 GHz and generating the radiation detection signals for each of the two or more frequencies and wherein the method further comprises determining a cross-correlation function of phase or amplitude associated with each of the two or more frequencies.

19. A method for non-invasive in-vivo assessment of at least one physiological condition of tissue, comprising:
monitoring at least one circulatory physiological parameter of the subject to generate one or more physiological signals, wherein the physiological parameter is indicative of temporal variations in blood circulation within a tissue portion containing a target tissue of interest,
irradiating the tissue portion with electromagnetic radiation having a frequency in a range of about 0.01 GHz to about 10 GHZ,
detecting at least a portion of the radiation transmitted or reflected by the irradiated tissue to generate one or more detected radiation signals,
synchronizing the detected radiation signals with the physiological signals, and processing the synchronized detected radiation signals and the physiological signals to obtain information regarding a physiological condition within the target tissue,
wherein the processing step comprises computing a cross correlation function of amplitude between an amplitude of the at least one of the detected radiation signals and an amplitude of the at least one of the physiological signals,
wherein the step of irradiating the tissue comprises irradiating the tissue at two or more frequencies in the frequency range of about 0.01 GHz to about 10 GHz and generating the radiation detection signals for each of the two or more frequencies and wherein the method further comprises determining a cross-correlation function of phase or amplitude associated with each of the two or more frequencies, and
further comprising identifying a hypoxic tissue condition based on observing a change in the cross-correlation function of amplitude without a substantial change in the cross-correlation function of phases.

20. A method for non-invasive in-vivo assessment of at least one physiological condition of tissue, comprising:
monitoring at least one circulatory physiological parameter of the subject to generate one or more physiological signals, wherein the physiological parameter is indicative of temporal variations in blood circulation within a tissue portion containing a target tissue of interest,
irradiating the tissue portion with electromagnetic radiation having a frequency in a range of about 0.01 GHz to about 10 GHZ,
detecting at least a portion of the radiation transmitted or reflected by the irradiated tissue to generate one or more detected radiation signals,
synchronizing the detected radiation signals with the physiological signals, and
processing the synchronized detected radiation signals and the physiological signals to obtain information regarding a physiological condition within the target tissue,
wherein the processing step comprises computing a cross correlation function of amplitude between an amplitude of the at least one of the detected radiation signals and an amplitude of the at least one of the physiological signals, wherein the step of irradiating the tissue comprises irradiating the tissue at two or more frequencies in the frequency range of about 0.01 GHz to about 10 GHz and generating the radiation detection signals for each of the two or more frequencies and wherein the method further comprises determining a cross-correlation function of phase or amplitude associated with each of the two or more frequencies, and further comprising identifying an ischemic tissue condition based on observing a change in a direction opposite to a direction of change associated with a hypoxic condition in the cross-correlation function of amplitude and a frequency and temporal-dependent change in the cross-correlation function of phase.

* * * * *